(12) United States Patent
Negishi et al.

(10) Patent No.: US 7,919,197 B2
(45) Date of Patent: Apr. 5, 2011

(54) CONDENSED RING AROMATIC COMPOUND AND ORGANIC LIGHT-EMITTING DEVICE HAVING THE SAME

(75) Inventors: Chika Negishi, Yokosuka (JP); Akihito Saitoh, Yokohama (JP); Hiroki Ohrui, Kawasaki (JP); Hironobu Iwawaki, Yokohama (JP); Masanori Muratsubaki, Hachioji (JP)

(73) Assignee: Canon Kabushiki Kaisha, Tokyo (JP)

( * ) Notice: Subject to any disclaimer, the term of this patent is extended or adjusted under 35 U.S.C. 154(b) by 312 days.

(21) Appl. No.: 12/301,434

(22) PCT Filed: Mar. 27, 2008

(86) PCT No.: PCT/JP2008/056615
§ 371 (c)(1),
(2), (4) Date: Nov. 18, 2008

(87) PCT Pub. No.: WO2008/120806
PCT Pub. Date: Oct. 9, 2008

(65) Prior Publication Data
US 2009/0184630 A1 Jul. 23, 2009

(30) Foreign Application Priority Data

Apr. 2, 2007 (JP) .............................. 2007-096343
Feb. 20, 2008 (JP) .............................. 2008-038298

(51) Int. Cl.
| | |
|---|---|
| H01L 51/54 | (2006.01) |
| H01J 1/63 | (2006.01) |
| C07C 13/465 | (2006.01) |
| C07C 211/43 | (2006.01) |
| C07C 25/22 | (2006.01) |
| C07C 43/20 | (2006.01) |
| C07D 213/04 | (2006.01) |
| C07D 401/14 | (2006.01) |

(52) U.S. Cl. ........ 428/690; 428/917; 546/255; 546/167; 570/183; 568/633; 564/426; 585/27; 313/504; 313/506

(58) Field of Classification Search ....................... None
See application file for complete search history.

(56) References Cited

U.S. PATENT DOCUMENTS

| | | | |
|---|---|---|---|
| 2004/0076853 A1 | 4/2004 | Jarikov | 428/690 |
| 2006/0210830 A1 | 9/2006 | Funahashi et al. | 428/690 |
| 2008/0124577 A1 | 5/2008 | Saitoh et al. | 428/704 |
| 2009/0033210 A1 | 2/2009 | Saitoh et al. | 313/504 |

FOREIGN PATENT DOCUMENTS

| | | |
|---|---|---|
| JP | 09-241629 | 9/1997 |
| JP | 10-189247 | 7/1998 |
| JP | 10-294177 | 11/1998 |
| JP | 2001-102173 | 4/2001 |
| JP | 2003-238516 | 8/2003 |

OTHER PUBLICATIONS

Kung K. Wang et al., "Thermolysis of Benzoenyne—Allenes to Form Biradicals and Subsequent Intramolecular Trapping with a Teraarylallene to Generate Two Triarylmethyl Radical Centers," J. Org. Chem., 1999, vol. 64, No. 5, pp. 1650-1656.

Norio Miyaura et al., "Palladium-Catalyzed Cross-Coupling Reactions of Organoboron Compounds," Chemical Reviews, 1995, vol. 95, No. 7, pp. 2457-2483.

Takakazu Yamamoto et al., "A Novel Type of Polycondensation Utilizing Transition Metal-Catalyzed C-C Coupling," Bulletin of the Chemical Society of Japan, Jul. 1978, vol. 57, No. 7, pp. 2091-2097.

Hermann A. Wegner et al., "A New Suzuki—Heck—Type coupling Cascade: Indeno[1,2,3]- Annelation of Polycyclic Aromatic Hydrocarbons," J. Org. Chem., 2003, vol. 68, No. 3, pp. 883-887.

Leo A. Paquette et al., "Regio- and Stereochemical Definition of Silatropic Migration within Trimethylsilyl-Substituted Isodicyclopentadienes," J. Am. Chem. Soc., vol. 105, No. 25 pp. 7364-7375.

Jiro Tatsugi et al., "A Convenient One-Pot Synthesis of Acenaphthenquinones from 1-Acenaphthenones by NBS-DMSO Oxidation," Bulletin of the Chemical Society of Japan, Oct. 1986, vol. 59, No. 10, pp. 3311-3313.

Christine Viala et al., "Synthesis of Polyaromatic Hydrocarbons with a Central Rotor," Eur. J. Org. Chem. 2002, pp. 4185-4189.

Jeff D. Debad et al., "Anodic Coupling of Diphenylbenzo[k]flouranthene: Mechanistic and Kinetic Studies Utilizing Cyclic Voltammetry and Electrogenerated Chemiluminescence," J. Org. Chem., 1997, vol. 62, No. 3, pp. 530-537.
Steven L. Murov et al., "Photophysics of Organic Molecules in Solution," Handbook of Photochemistry (Second Edition, Revised and Expanded) pp. 1-3 and 26-27.
Axel D. Becke., "Density-Functional Thermochemistry. III. The Role of Exact Exchange," J. Chem. Phys., Apr. 1,1993, vol. 98, No. 7, pp. 5648-5652.
Kung K. Wang et al., "Thermolysis of Benzoenyne-Allenes to Form Biradicals and Subsequent Intramolecular Trapping with a Tetraarylallene to Generate Two Triarylmethyl Radical Centers," J. Org. Chem., vol. 64, pp. 1650-1656 (1999).
Russian Office Action issued in counterpart application No. 2009140295 dated Aug. 18, 2010, along with English-language translation—8 pages.
International Preliminary Report on Patentability for PCT/JP2008/056615 dated Oct. 15, 2009, 6 pages.

*Primary Examiner* — Dawn Garrett
(74) *Attorney, Agent, or Firm* — Fitzpatrick, Cella, Harper & Scinto

(57) ABSTRACT

There are provided a condensed ring aromatic compound and an organic light-emitting device having an optical output with high efficiency and high luminance, and durability. An organic light-emitting device including: a pair of electrodes comprising an anode and a cathode of which at least one is transparent or translucent; and an organic compound layer disposed between the pair of electrodes, wherein the organic compound layer contains the condensed ring aromatic compound represented by the following formula [1].

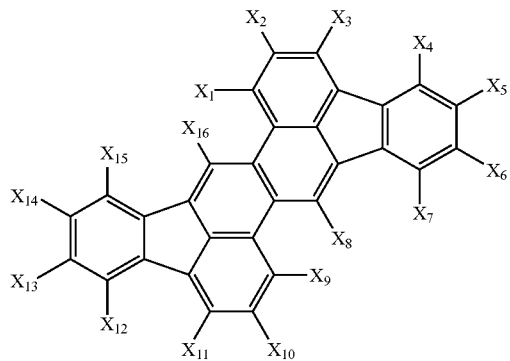

In the formula, $X_1$ to $X_{16}$ each independently represent a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and each may be the same or different; adjacent groups combine with each other to form at least one ring in the group selected from $X_4$ to $X_7$; and adjacent groups combine with each other to form at least one ring in the group selected from $X_{12}$ to $X_{15}$.

6 Claims, 3 Drawing Sheets

CONDENSED RING AROMATIC COMPOUND AND ORGANIC LIGHT-EMITTING DEVICE HAVING THE SAME

TECHNICAL FIELD

The present invention relates to a novel condensed ring aromatic compound and an organic light-emitting device having the same.

BACKGROUND ART

An organic light-emitting device is a device for sandwiching a thin film including a fluorescent organic compound between an anode and a cathode. In addition, an organic light-emitting device emits light when an exciton of a fluorescent organic compound is formed by injecting an electron and a hole from each electrode, and this exciton returns to a ground state.

Recent progress in an organic light-emitting device is remarkable and its characteristics include, for example, high luminance at a low applied voltage, diversity of light-emitting wavelengths, high-speed responsibility, and providing a thin and lightweight light-emitting device. From these characteristics, a possibility is suggested that an organic light-emitting device is used for wide range of applications.

However, an organic light-emitting device having an optical output of higher luminance or higher conversion efficiency is necessary under present circumstances. Further, an organic light-emitting device still has many problems in terms of durability such as change over time due to use for a long period of time and deterioration due to atmosphere gas containing oxygen, moisture or the like.

Therefore, a material for realizing an organic light-emitting device having high light-emitting efficiency and good durability has been demanded in recent years.

As a method for solving the above-mentioned problems, it has been proposed that a condensed ring aromatic compound is used as a material for constituting an organic light-emitting device. Japanese Patent Application Laid-Open No. 2001-102173, U.S. Patent Application Publication No. 2004-0076853, Japanese Patent Application Laid-Open No. 2006-256979, Japanese Patent Application Laid-Open Nos. H10-189247, and H09-241629 disclose examples of using a condensed ring aromatic compound as a material for constituting an organic light-emitting device. In addition, J. Org. Chem. 64, 1650-1656, 1999 also discloses a condensed ring aromatic compound.

DISCLOSURE OF THE INVENTION

The present invention has been made to solve the problems of prior arts as described above. That is, an object of the present invention is to provide a novel condensed ring aromatic compound for an organic light-emitting device. Further, another object of the present invention is to provide an organic light-emitting device having an optical output with high efficiency and high luminance, and durability.

The present inventors have made investigation to solve the above-mentioned problems, consequently leading to the completion of the present invention. That is, a condensed ring aromatic compound of the present invention is represented by the following general formula [1]:

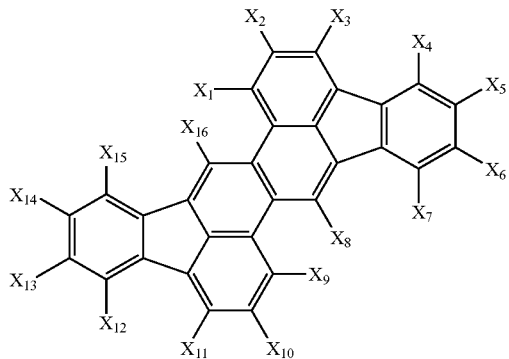

wherein $X_1$ to $X_{16}$ each independently represent a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and each may be the same or different; adjacent groups combine with each other to form at least one ring in the group selected from $X_4$ to $X_7$; and adjacent groups combine with each other to form at least one ring in the group selected from $X_{12}$ to $X_{15}$.

A novel condensed ring aromatic compound of the present invention has high quantum efficiency. Therefore, according to the present invention, an organic light-emitting device having an optical output with high efficiency and high luminance, and durability can be provided.

Further feature of the present invention will become apparent from the following description of exemplary embodiments with reference to the attached drawings.

BEST MODES FOR CARRYING OUT THE INVENTION

Figure 1:
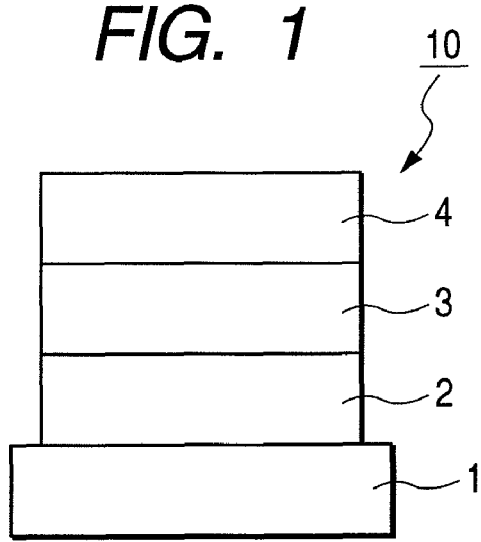
FIG. 1 is a cross-sectional view showing a first embodiment in an organic light-emitting device of the present invention.

A condensed ring aromatic compound of the present invention will be described in detail. The condensed ring aromatic compound of the present invention is represented by the following general formula [1]:

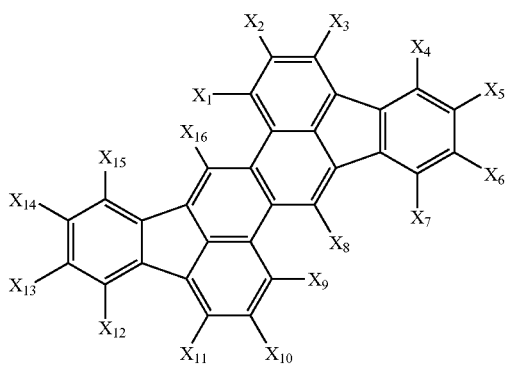

[1]

wherein $X_1$ to $X_{16}$ each independently represent a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and each may be the same or different; adjacent groups combine with each other to form at least one ring in the group selected from $X_4$ to $X_7$; and adjacent groups combine with each other to form at least one ring in the group selected from $X_{12}$ to $X_{15}$.

Further, the condensed ring aromatic compound of the present invention is the condensed ring aromatic compound according to the above-mentioned general formula [1], represented by the following general formula [2]:

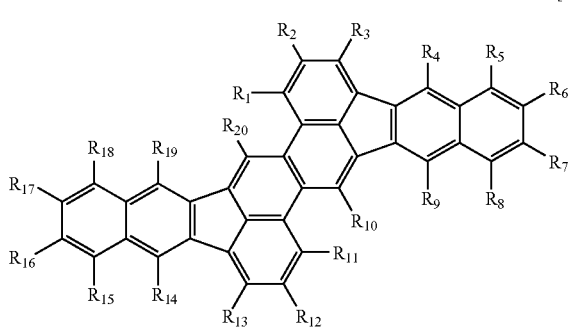

[2]

wherein $R_1$ to $R_{20}$ each independently represent a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and each may be the same or different.

Specific examples of substituents represented by $X_1$ to $X_{16}$ and $R_1$ to $R_{20}$ in the above-mentioned general formulas [1] and [2], respectively, will be described below, but are not limited to these substituents.

Examples of halogen atoms represented by $X_1$ to $X_{16}$ and $R_1$ to $R_{20}$ include fluorine, chlorine, bromine and iodine.

Examples of alkyl groups represented by $X_1$ to $X_{16}$ and $R_1$ to $R_{20}$ include a methyl group, an ethyl group, a normal propyl group, isopropyl group, a normal butyl group, a tertiary butyl group, a secondary butyl group, a normal pentyl group, an octyl group, a 1-adamantyl group, a 2-adamantyl group, a benzyl group and a phenetyl group.

Examples of alkoxy groups represented by $X_1$ to $X_{16}$ and $R_1$ to $R_{20}$ include a methoxy group, an ethoxy group, a propoxy group, a 2-ethyl-octyloxy group and a benzyloxy group.

Examples of aryloxy groups represented by $X_1$ to $X_{16}$ and $R_1$ to $R_{20}$ include a phenoxy group, 4-tertiary-butylphenoxy group and a thienyloxy group.

Examples of amino groups represented by $X_1$ to $X_{16}$ and $R_1$ to $R_{20}$ include an N-methylamino group, an N-etylamino group, an N-N-dimethylamino group, an N-N-dietylamino group, an N-methyl-N-ethylamino group, an N-benzylamino group, an N-methyl-N-benzylamino group, an N,N-dibenzylamino group, an anilino group, an N,N-diphenylamino group, an N,N-dinaphtylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesithylamino group, an N-phenyl-N-(4-tertiary-butylphenyl)amino group, an N-phenyl-N-(4-trifluoromethylphenyl)amino group, an N,N-di(4-tertiary-butylphenyl)amino group, an N-N-di(3,5-dimethylphenyl) amino group, an N-(9,9-dimethyl-fluorenyl)-N-phenylamino group, an N-(9,9-dimethyl-fluorenyl)-N-tolylamino group, an N-(9,9-dimethyl-fluorenyl)-N-(3,5-dimethylphenyl) amino group, and an N-(9,9-dimethyl-fluorenyl)-N-(2-naphthyl)amino group.

Examples of aryl groups represented by $X_1$ to $X_{16}$ and $R_1$ to $R_{20}$ include a phenyl group, a naphthyl group, a pentalenyl group, an indenyl group, an azulenyl group, an anthryl group, a pyrenyl group, an indacenyl group, an acenaphtenyl group, a phenantryl group, a phenalenyl group, a fluorantenyl group, an acephenanthryl group, an aceanthryl group, a triphenylenyl group, a crycenyl group, a naphthacenyl group, a perylenyl group, a pentacenyl group, a biphenyl group, a terphenyl group and a fluorenyl group.

Examples of heterocyclic groups represented by $X_1$ to $X_{16}$ and $R_1$ to $R_{20}$ include a pyridyl group, a bipyridyl group, a pyrrolyl group, an oxazolyl group, an oxadiazolyl group, a thiazolyl group, a thiadiazolyl group, a quinolyl group, an isoquinolyl group, a carbazolyl group, an acrydinyl group and a phenanthoryl group.

Examples of substituents which the above-mentioned alkyl group, aryl group and heterocyclic group may have include alkyl groups such as a methyl group, an ethyl group and a propyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, a ditolylamino group and a dianisolylamino group; alkoxy groups such as a methoxy group, an ethoxy group and a propoxy group; aryloxy groups such as a phenoxyl group; halogen atoms such as fluorine, chlorine, bromine and iodine; and cyano groups.

The condensed ring aromatic compound represented by the general formulas [1] and [2] can be synthesized, for example, by a method as shown in the following synthesis routes 1 and 2.

Synthesis Route 1

The condensed ring aromatic compound represented by the general formula [1] can be synthesized, for example, by using a dibromochrysene derivative and a boronic acid derivative for raw materials as shown in the following synthesis route 1, but the synthesis method is not limited to this route 1.

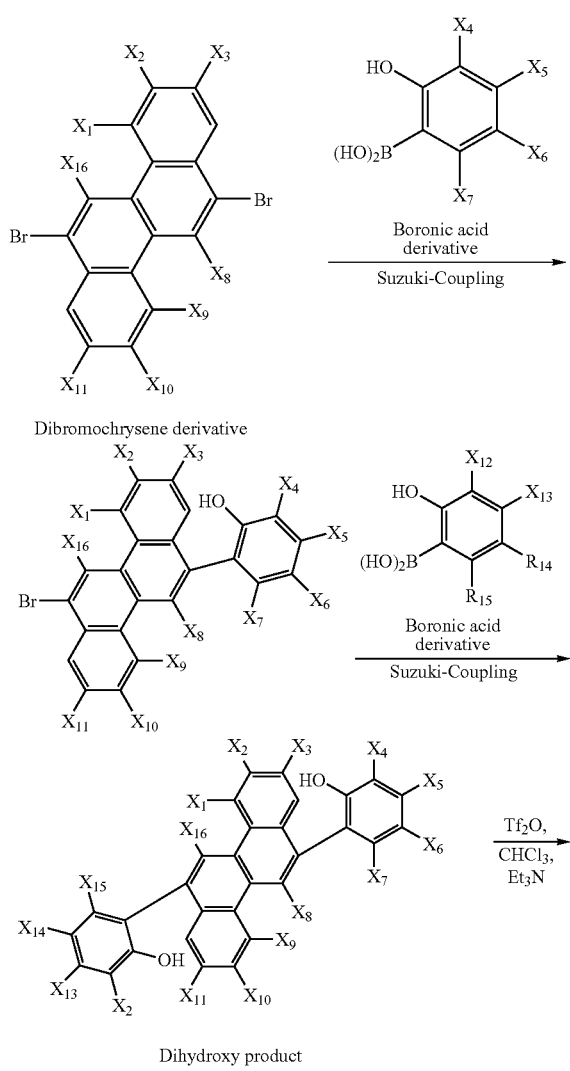

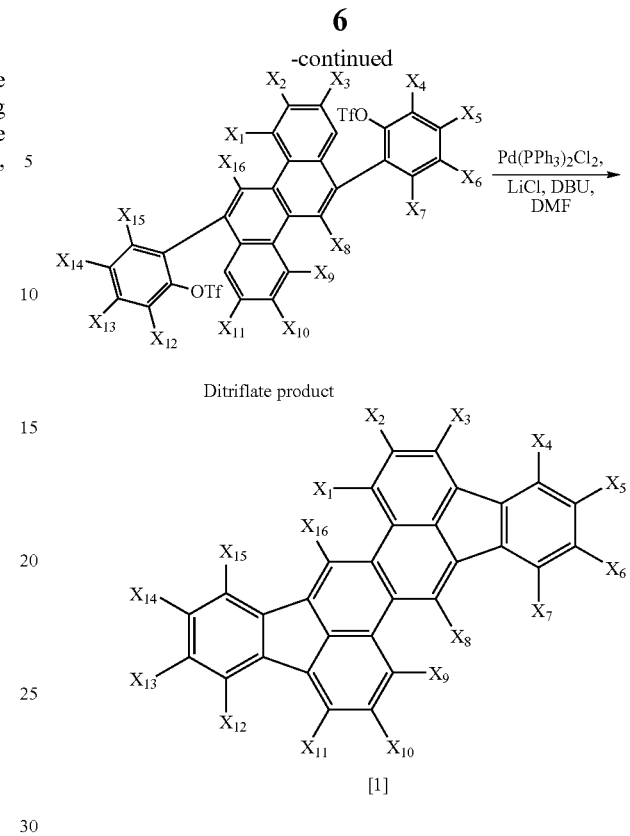

Specific method of the synthesis route 1 will be described. Firstly, a dihydroxy product is synthesized by Suzuki-Miyaura-coupling reaction between a dibromochrysene derivative and a boronic acid derivative (for example, Chem. Rev. 1995, 95, 2457-2483). Another method includes, for example, Yamamoto method using a nickel catalyst (for example, Bull. Chem. Soc. Jpn. 51, 2091, 1978). Next, a ditriflate product is derived from the synthesized dihydroxy product and is subjected to intramolecular cyclization (for example, J. Org. Chem. 68, 883-887, 2003). Thereby, the condensed ring aromatic compound represented by the general formula [1] can be obtained.

Synthesis Route 2

The condensed ring aromatic compound represented by the general formula [2] can also be synthesized, for example, by using a dibromochrysene derivative for a raw material as shown in the following synthesis route 2.

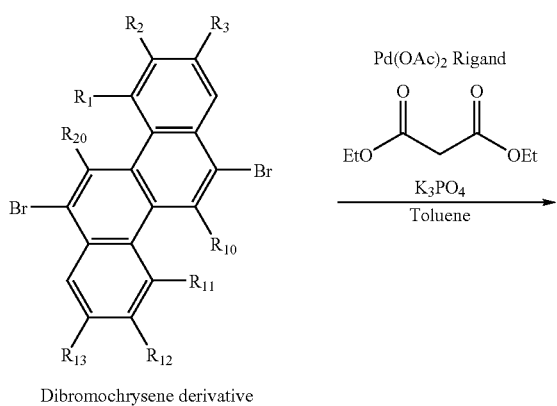

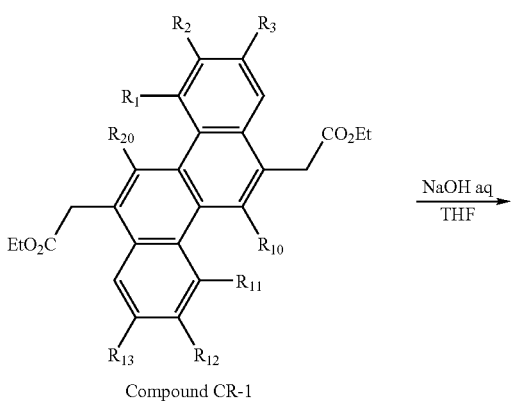

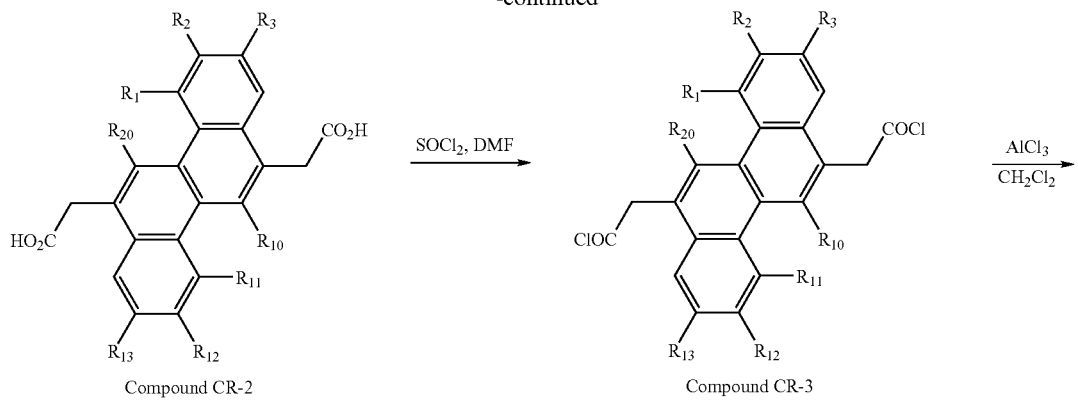
Compound CR-2 → Compound CR-3 (SOCl$_2$, DMF); Compound CR-3 → (AlCl$_3$, CH$_2$Cl$_2$)
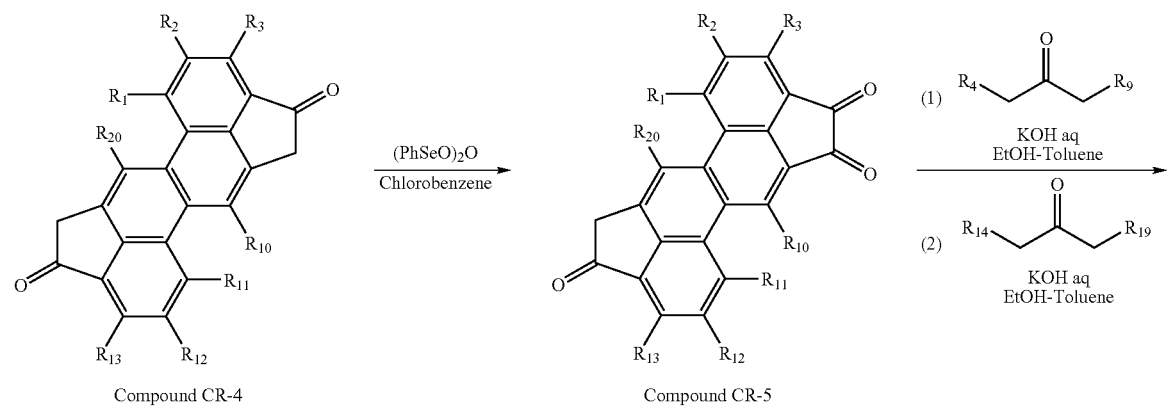
Compound CR-4 → Compound CR-5 ((PhSeO)$_2$O, Chlorobenzene) → (1) R$_4$COCH$_2$R$_9$ ketone, KOH aq, EtOH-Toluene; (2) R$_{14}$COCH$_2$R$_{19}$ ketone, KOH aq, EtOH-Toluene
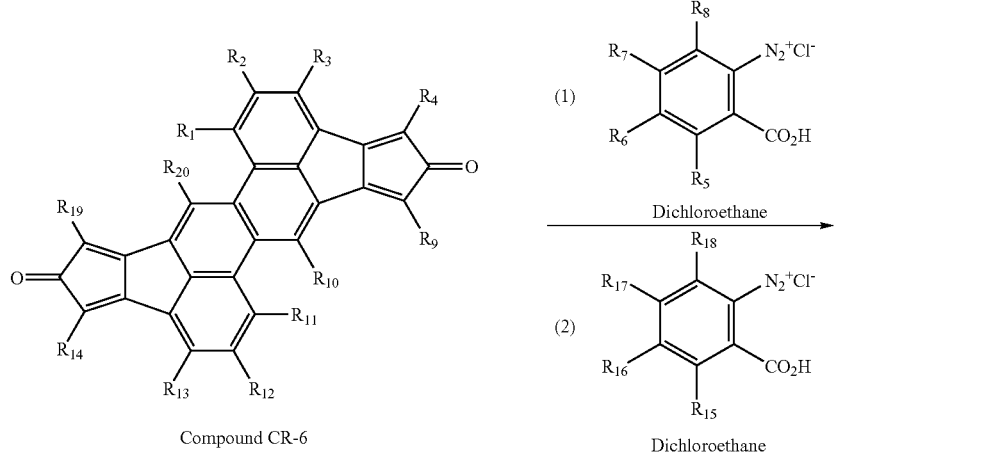
Compound CR-6 → (1) diazonium/benzoic acid reagent, Dichloroethane; (2) diazonium/benzoic acid reagent, Dichloroethane
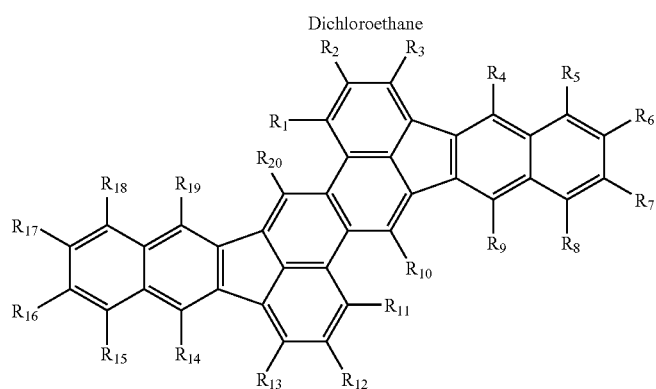
[2]

Specific method of the synthesis route 2 will be described.

The synthesis route 2 is especially useful when various substituents are introduced into $R_4$ to $R_9$ or $R_{14}$ to $R_{19}$ in the general formula [2]. Specifically, a dibromochrysene derivative is derived to a compound CR-1 that is an ester product thereof. Next, the ester product is subjected to hydrolysis to derive a compound CR-2, and the compound CR-2 is derived to a compound CR-3 that is an acid chloride thereof via a subsequent process. The compound CR-3 is further subjected to intramolecular cyclization (for example, J. Am. Chem. Soc. 105, 7375, 1983) to thereby derive a ketone product. This ketone product is converted to a diketone product (for example, Bull. Chem. Soc. Jpn. 59, 3311, 1986). This diketone product is used as an intermediate and various substituents are introduced into $R_4$ to $R_9$ or $R_{14}$ to $R_{19}$ via two processes of Knoevenagel reaction (for example, Eur. J. Org. Chem. 4185, 2002) and Diels-Alder reaction (for example, J. Org. Chem. 62, 530, 1997).

A material used for an organic light-emitting device has desirably high light-emitting quantum efficiency when using as light-emitting center material.

The compound of the general formula [1] is a compound obtained by forming a condensed ring in a compound A having high light-emitting quantum efficiency shown below.

Compound A

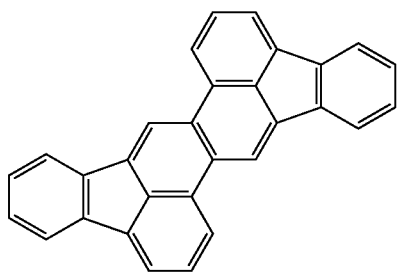

Exemplified Compound B-1

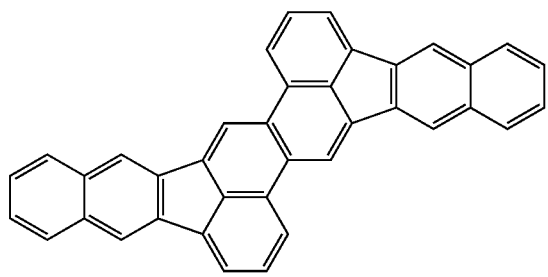

The compound A shows a high light-emitting quantum efficiency of 0.91 in a toluene solution ($1\times10^{-5}$ mol/L). The light-emitting quantum efficiency was relatively calculated using fluorantene as a control compound in measurement. It is to be noted that fluorantene in the dilute solution has a light-emitting quantum efficiency of 0.35 (Steven L, Murov., Handbook of Photochemistry, Second Edition, Revised and Exapanded, (1993)).

Accordingly, the compound represented by the general formula [1] gains increased oscillator strength by expansion of a π-conjugated system of the compound A, and therefore can be expected to further improve light-emitting quantum efficiency.

The present inventors calculated oscillator strengths of compounds represented by the compound A and the exemplified compound B-1, for example, by simulation of calculation, so that the oscillator strengths of 0.44 and 0.78, respectively, were obtained.

In this case, the simulation of calculation was performed using a B3LYP method (Becke's Three parameter hybrid method using the Lee-Yang-Parr correlation (J. Chem. Phys. 98, 5648 (1993))), one of density functional methods of Gaussian 03 package (Gaussian, Inc.) that is a molecular orbital calculation program.

Further, introduction of a substituent into any one of $X_1$ to $X_{16}$ in the general formula [1] can suppress association of molecules themselves to lower reduction in light-emitting efficiency. By doing this, light-emitting efficiency can be expected to be further improved. Especially, when a substituent is introduced into $X_1$, $X_4$, $X_7$, $X_8$, $X_9$, $X_{12}$, $X_{15}$ or $X_{16}$, the substituent tends to position in a direction perpendicular to a plane of the compound of the general formula [1] due to steric hindrance between adjacent substituents, and thereby an effect of lowering reduction in light-emitting efficiency due to the molecular association is large.

Examples of a substituent giving steric hindrance to a molecule itself include an alkyl group, an alkoxy group, an aryloxy group, an amino group, an aryl group and a heterocyclic group, and preferable examples thereof include an amino group, an aryl group and a heterocyclic group.

When the compound represented by the general formula [1] is used as a light-emitting layer, it can be used as either a host material or a guest material. Especially, when the compound represented by the general formula [1] is used as a host material of a light-emitting layer, the compound is preferably a material having a high glass transition temperature, and for that purpose, it is desirable that $X_1$ to $X_{16}$ have substituents.

Preferable examples of substituents of $X_1$ to $X_{16}$ for increasing the glass transition temperature include an amino group, an aryl group and a heterocyclic group.

Further, a substituent introduced for using the compound represented by the general formula [1] as an intermediate of a synthesis process includes, for example, a halogen atom. In this case, iodine, bromine and chlorine are preferred from the viewpoint of activity in a synthesis reaction.

A compound used as a material of an organic light-emitting device desirably has a high carrier injecting property. A device can be driven at a lower voltage by facilitating carrier injection. Preferable examples of a substituent introduced for enhancing carrier injecting property include an amino group and a heterocyclic group. In this case, when an amino group is introduced as a substituent, a hole injecting property is generally improved. On the other hand, when a heterocyclic group is introduced, electron injecting property is improved.

Specific examples of the compound in the above-mentioned general formula [1] are shown below. However, the present invention is not limited to these compounds.

B-1

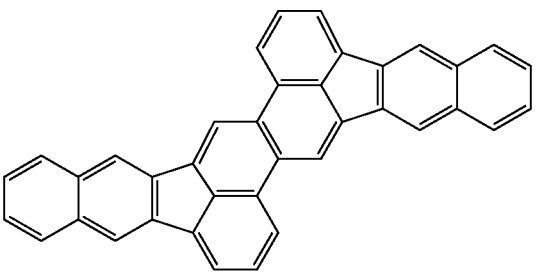

C-1
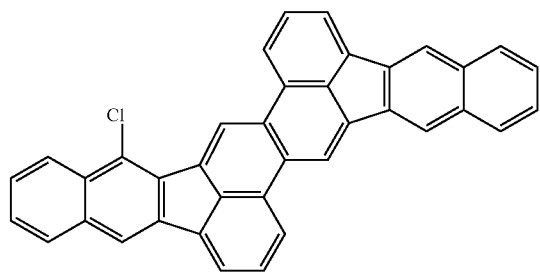
C-2
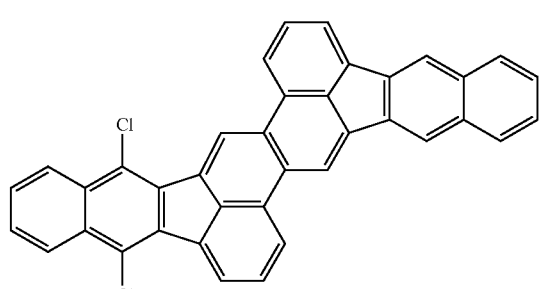
C-3
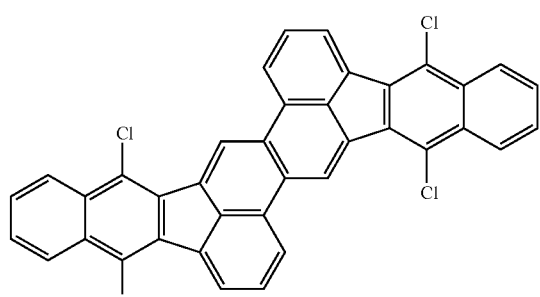
C-4
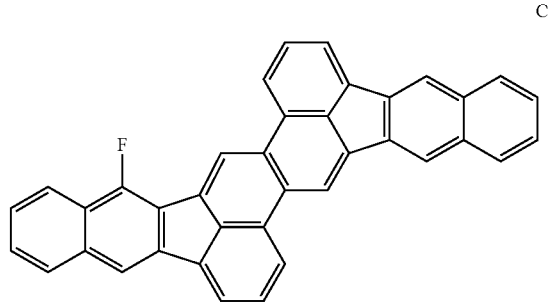
C-5
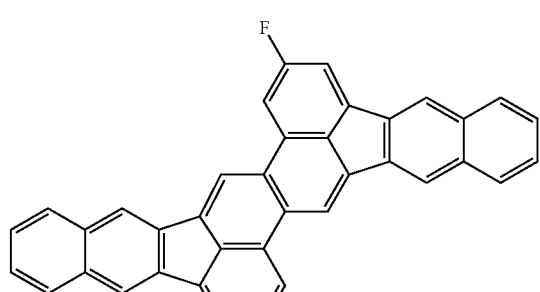
C-6
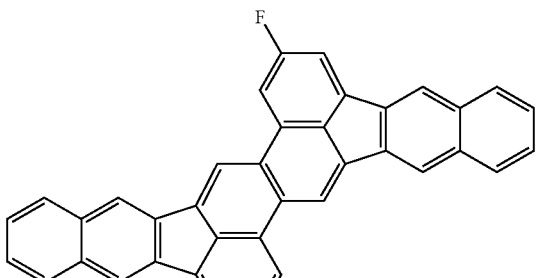
D-1
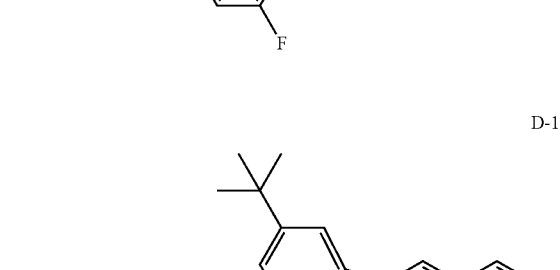
D-2
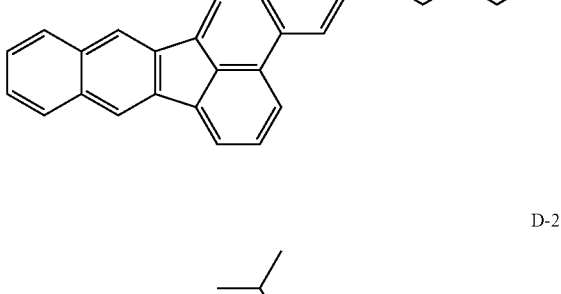
D-3
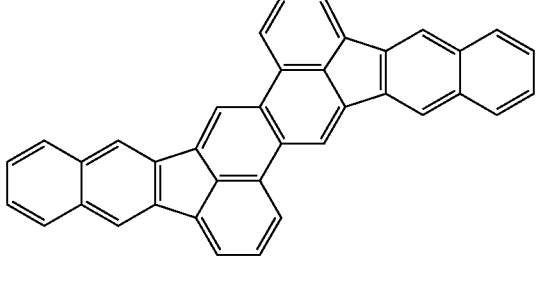

D-4
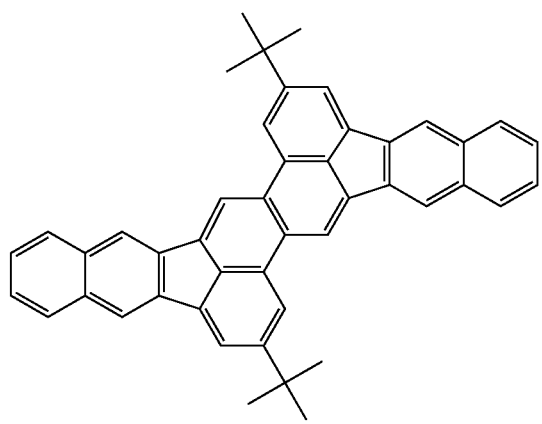
D-5
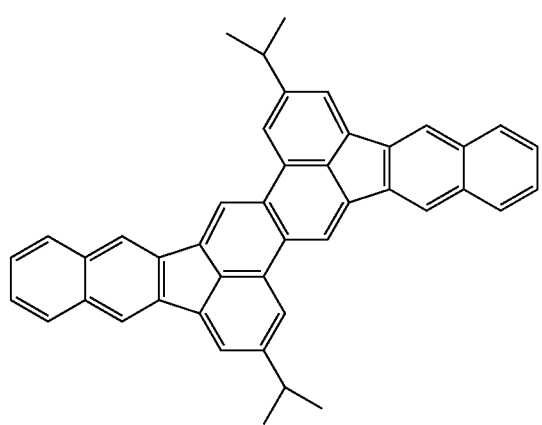
D-6
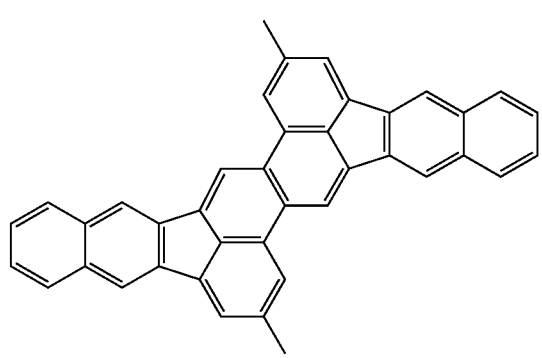
E-1
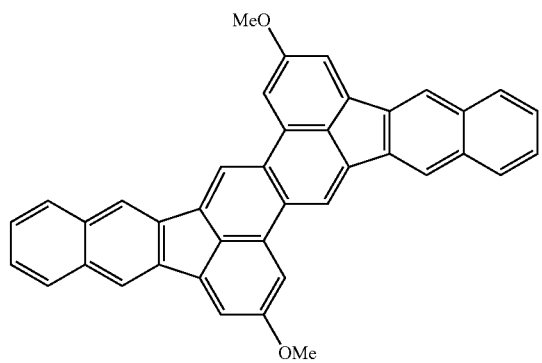
E-2
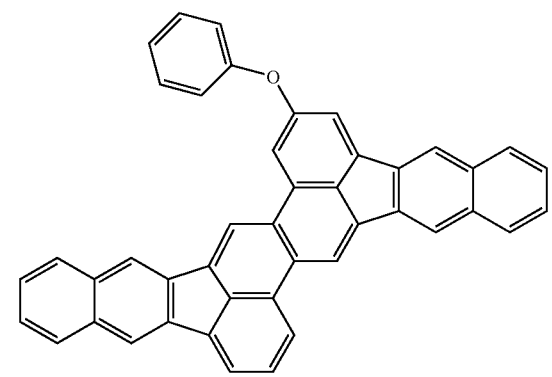
E-3
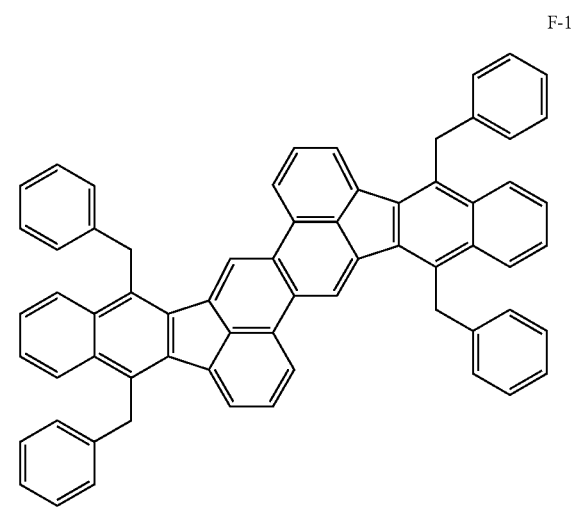
F-1

F-2
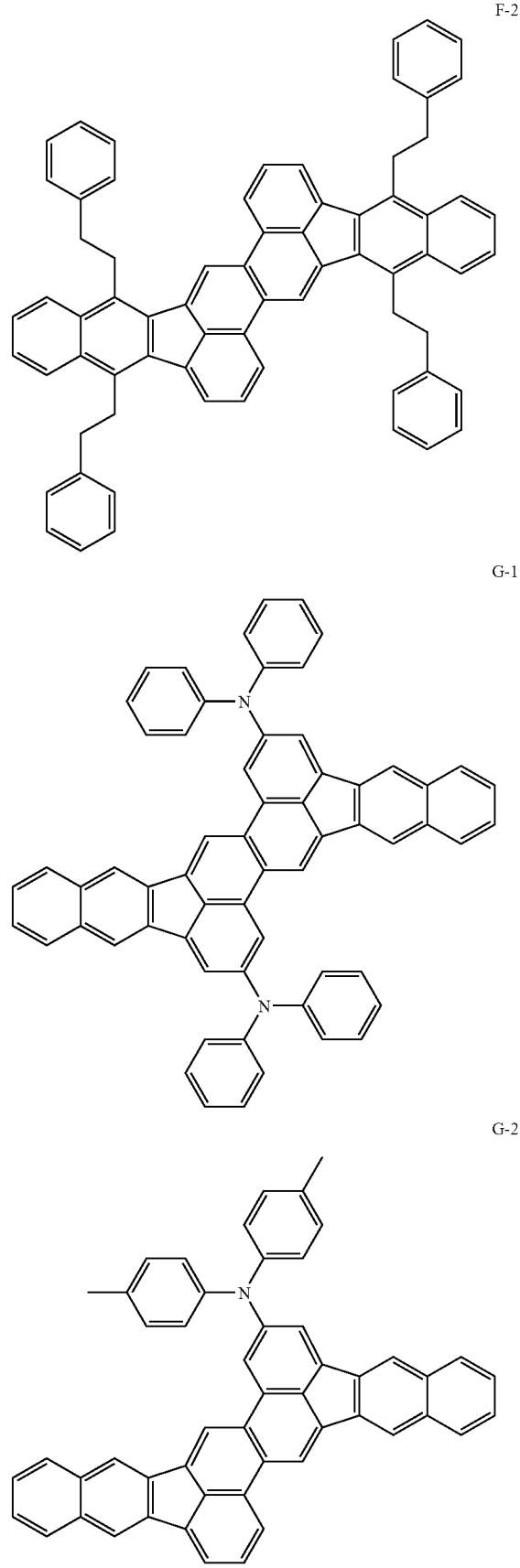
G-1
G-2
H-1
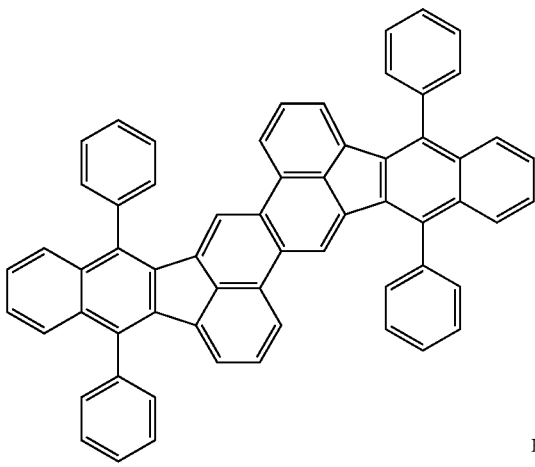
H-2
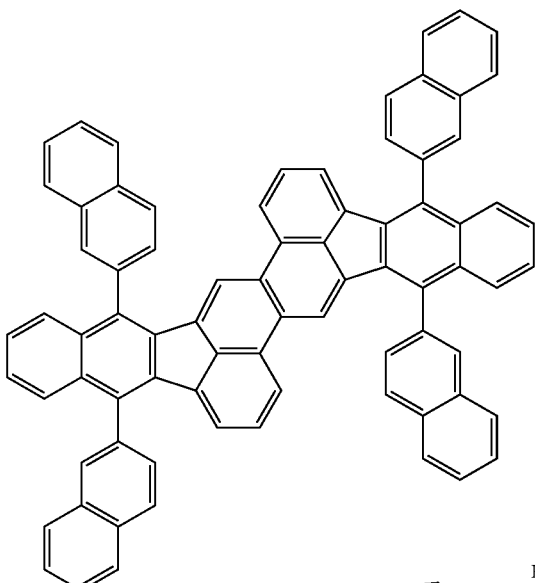
H-3
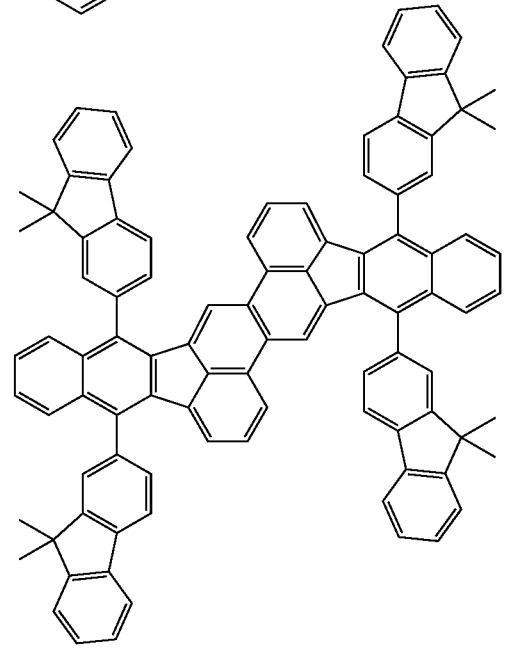

-continued
H-4
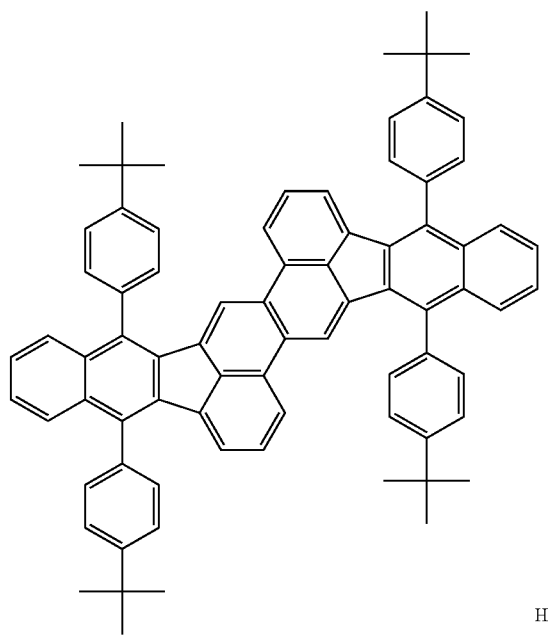
H-5
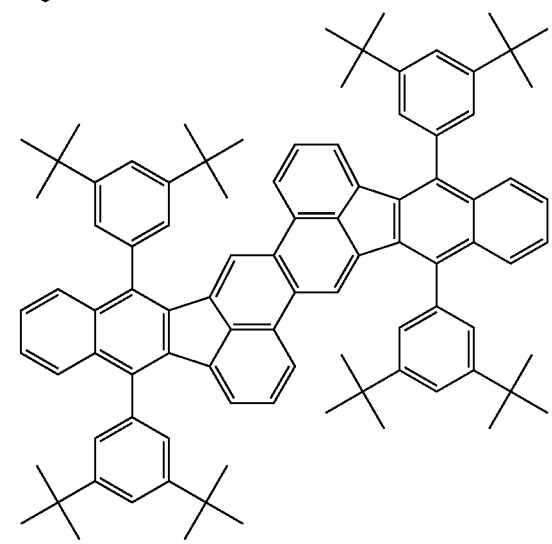
H-6
H-7
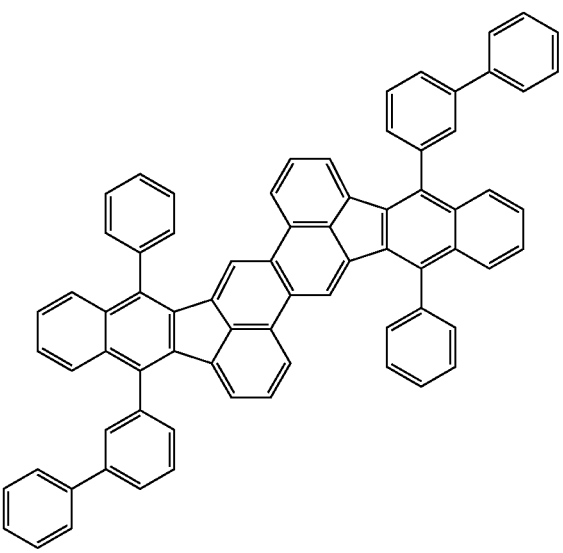
H-8
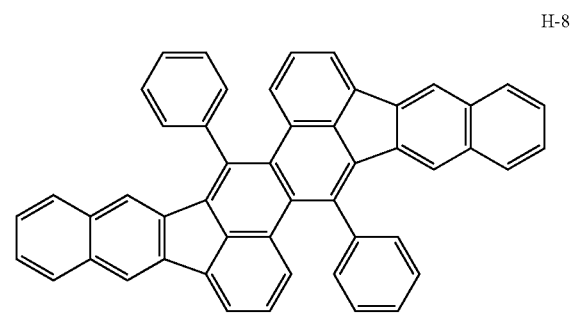
H-9
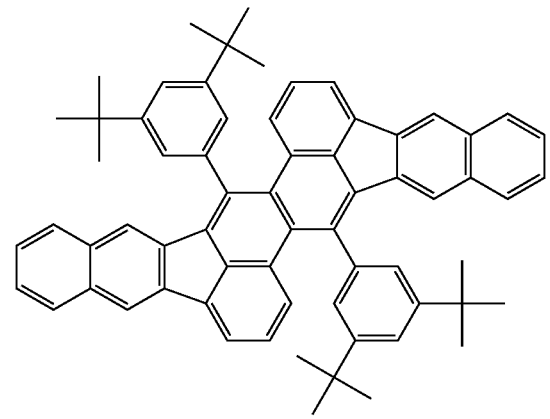

I-1
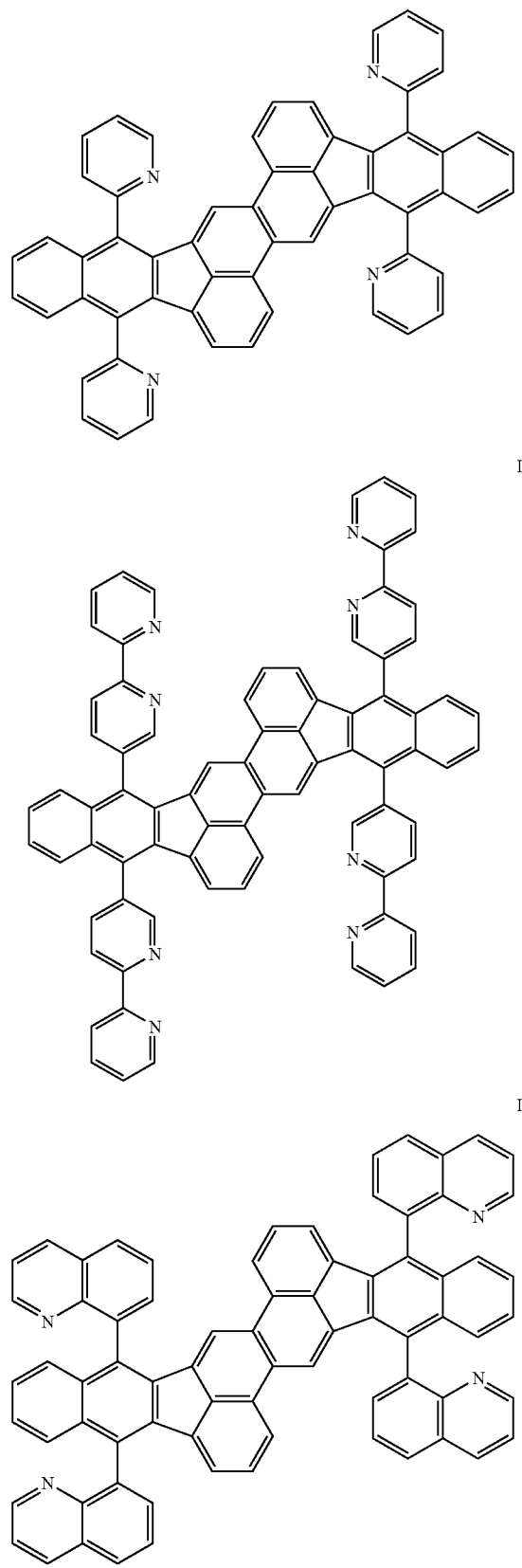
I-2
I-3
J-1
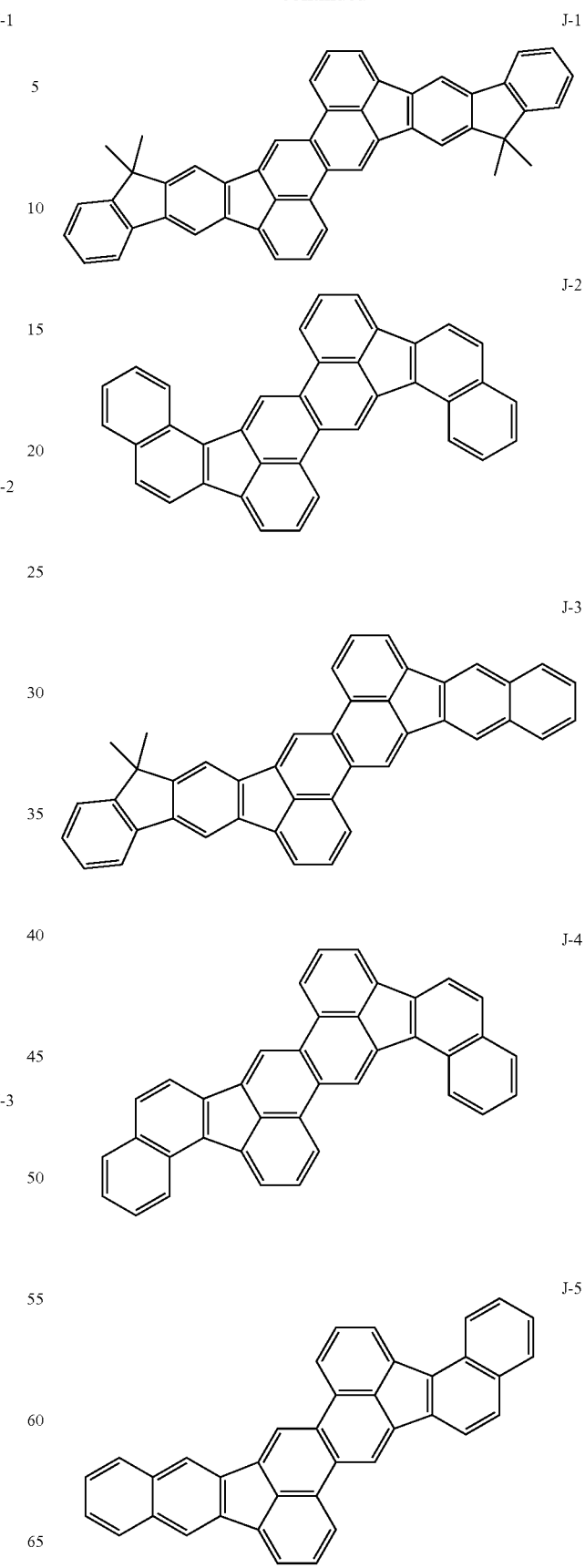
J-2
J-3
J-4
J-5

-continued

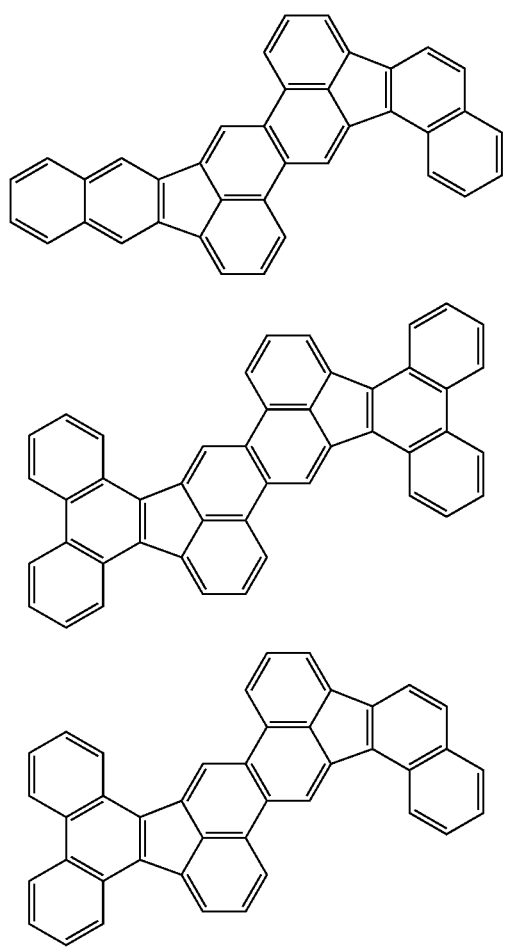

Next, an organic light-emitting device of the present invention will be described in detail.

The organic light-emitting device of the present invention includes an anode, a cathode and a layer comprising an organic compound (organic compound layer) sandwiched between the anode and the cathode. Further, in the organic light-emitting device of the present invention, the layer comprising an organic compound contains a condensed ring aromatic compound of the present invention.

The organic light-emitting device of the present invention may include other organic compound layers other than the organic compound layer disposed between the anode and the cathode which are a pair of electrodes. Other organic compound layers include, for example, a hole injecting layer, a hole transporting layer, an electron blocking layer, a hole blocking layer, an electron transporting layer and an electron injecting layer.

Hereinafter, the organic light-emitting device of the present invention will be described in detail with reference to drawings.

Firstly, reference numerals in drawings will be described. Reference numeral 1 denotes a substrate; 2, an anode; 3, a light-emitting layer; 4, an cathode; 5, a hole transporting layer; 6, electron transporting layer; 7, a hole injecting layer; 8, a hole/exciton blocking layer for blocking a hole and/or an exciton; and 10, 20, 30, 40, 50, organic light-emitting devices.

FIG. 1 is a cross-sectional view showing a first embodiment in an organic light-emitting device of the present invention. In an organic light-emitting device 10 of FIG. 1, an anode 2, a light-emitting layer 3 and a cathode 4 are sequentially disposed on a substrate 1. This organic light-emitting device 10 is useful when the light-emitting layer 3 comprises an organic compound having all of hole transporting capability, electron transporting capability and light-emitting performance. Further, the organic light-emitting device 10 is also useful when the light-emitting layer 3 comprises a mixture of organic compounds each having any one of characteristics of hole transporting capability, electron transporting capability and light-emitting performance.

Figure 2:
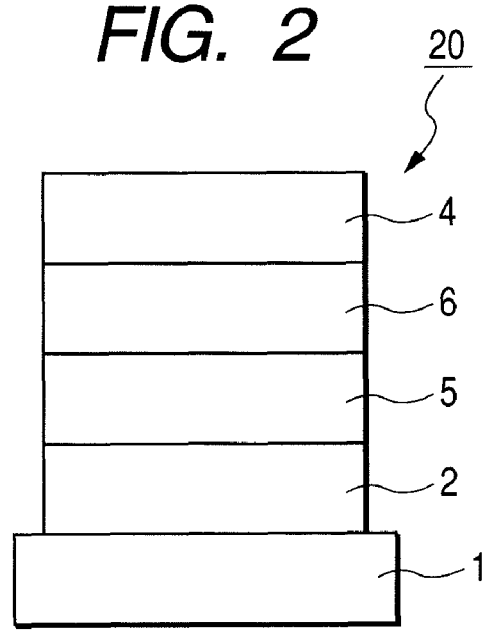
FIG. 2 is a cross-sectional view showing a second embodiment in an organic light-emitting device of the present invention.

FIG. 2 is a cross-sectional view showing a second embodiment in an organic light-emitting device of the present invention. In an organic light-emitting device 20 of FIG. 2, an anode 2, a hole transporting layer 5, an electron transporting layer 6 and a cathode 4 are sequentially disposed on a substrate 1. This organic light-emitting device 20 is useful when a light-emitting organic compound having any one of hole transporting property and electron transporting property is used in combination with an organic compound having only electron transporting property or hole transporting property. In addition, the hole transporting layer 5 or the electron transporting layer 6 is also served as a light-emitting layer in the organic light-emitting device 20.

Figure 3:
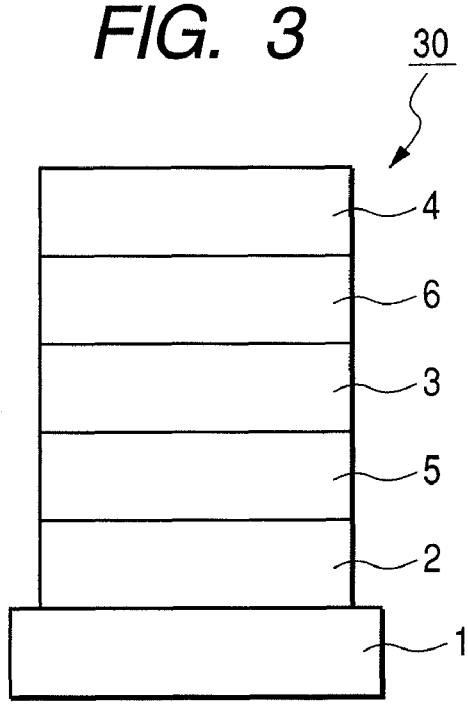
FIG. 3 is a cross-sectional view showing a third embodiment in an organic light-emitting device of the present invention.

FIG. 3 is a cross-sectional view showing a third embodiment in an organic light-emitting device of the present invention. An organic light-emitting device 30 of FIG. 3 is one in which a light-emitting layer 3 is interposed between the hole transporting layer 5 and the electron transporting layer 6 in the organic light-emitting device 20 of FIG. 2. This organic light-emitting device 30 has a carrier transporting function and a light-emitting function which are separated from each other, and organic compounds having each characteristics of hole transporting property, electron transporting property and light-emitting property can be used in appropriate combination. Therefore, degree of freedom of material selection is extremely increased and various organic compound having different light-emitting wavelengths can be used, thereby enabling diversification of light-emitting hues. In addition, the organic light-emitting device 30 can also be intended to improve the light-emitting efficiency by effectively trapping a carrier or an exciton in the light-emitting layer 3 in the center.

Figure 4:
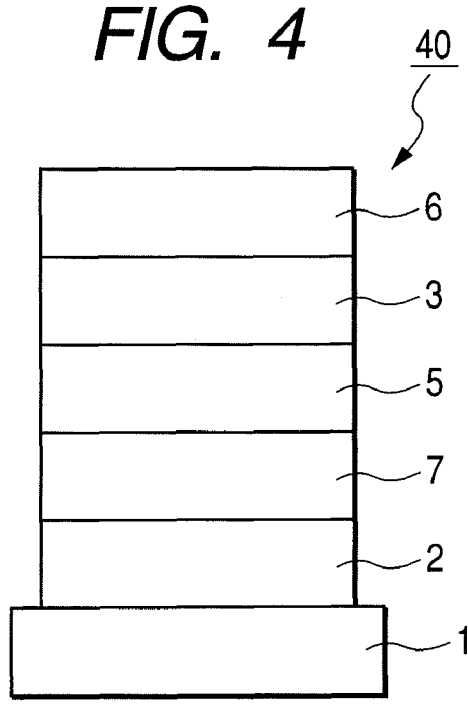
FIG. 4 is a cross-sectional view showing a fourth embodiment in an organic light-emitting device of the present invention.

FIG. 4 is a cross-sectional view showing a fourth embodiment in an organic light-emitting device of the present invention. An organic light-emitting device 40 of FIG. 4 is one in which a hole injecting layer 7 is disposed between the anode 2 and the hole transporting layer 5 in the organic light-emitting device 30 of FIG. 3. This organic light-emitting device 40 improves adhesion between the anode 2 and the hole transporting layer 5 or hole injecting property by disposing the hole injecting layer 7, and thereby is effective for voltage reduction.

Figure 5:
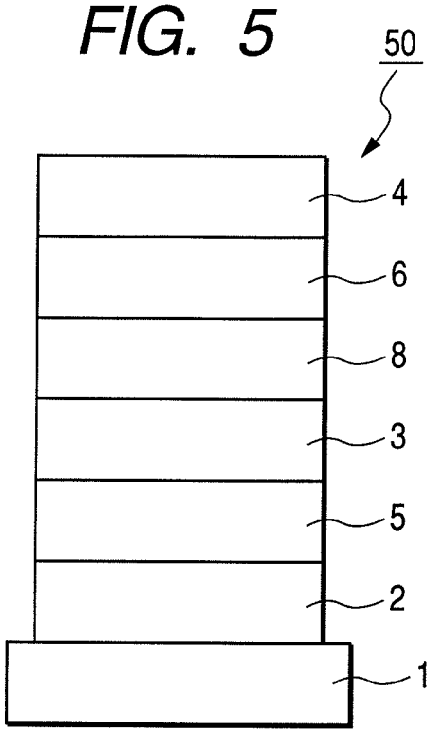
FIG. 5 is a cross-sectional view showing a fifth embodiment in an organic light-emitting device of the present invention.

FIG. 5 is a cross-sectional view showing a fifth embodiment in an organic light-emitting device of the present invention. An organic light-emitting device 50 of FIG. 5 is one in which a layer for preventing a hole or an exciton from passing through to a side of the cathode 4 (hole/exciton blocking layer 8) is interposed between the light-emitting layer 3 and the hole transporting layer 6 in the organic light-emitting device 30 of FIG. 3. Light-emitting efficiency of the organic light-emitting device 50 is improved by using an organic compound having an extremely high ionization potential as the hole/exciton blocking layer 8.

However, the first to fifth embodiments described above have only basic device structures and a structure of an organic light-emitting device using a condensed ring aromatic compound of the present invention is not limited to these embodiments. There can be employed various layer structures such as, for example, a layer structure in which an insulating layer, an adhesive layer or an interference layer is disposed at an interface between an electrode and an organic layer, and a layer structure in which a hole transporting layer comprises two layers having different ionization potentials.

The condensed ring aromatic compound of the present invention can be used for any one of the first to fifth embodiments. In addition, when the condensed ring aromatic compound of the present invention is used, a single compound may be used and a plurality of compounds may be used in combination.

Further, the condensed ring aromatic compound of the present invention is contained in a layer comprising an organic compound, for example, any one of the light-emitting layer 3, the hole transporting layer 5, the electron transporting layer 6, the hole injecting layer 7 and the hole/exciton blocking layer 8 in the first to fifth embodiments. It is preferably contained in the light-emitting layer 3. In addition, one kind or two or more kinds of the condensed ring aromatic compound of the present invention may be contained in these layers.

The light-emitting layer 3 preferably comprises a host and a guest. Herein, when the light-emitting layer 3 comprises a host and a guest having carrier transporting properties, the main process leading to light emission includes the following some processes.
1. Transportation of electron and hole in light-emitting layer
2. Formation of exciton of host
3. Transmission of excitation energy between host molecules
4. Transfer of excitation energy from host to guest Desired energy transfer or light emission in each of the processes occurs in competition with various deactivation processes.

It is needless to say that light-emitting quantum efficiency of a light-emitting center material itself is increased in order to enhance light-emitting efficiency of an organic light-emitting device. However, it has become a serious problem how energy transfer between a host and a host or between a host and a guest can be efficiently performed. In addition, although the cause of deterioration of light emission due to energization is not clear at the present time, it is supposed that the cause is associated with environmental change of a light-emitting material by at least a light-emitting center material itself or a molecule surrounding it.

Herein, when the condensed ring aromatic compound of the present invention is used for a host or a guest of a light-emitting layer, the light-emitting efficiency of a device, the luminance of light output by a device and the durability of a device are improved.

When the condensed ring aromatic compound of the present invention is used as a light-emitting layer material for the organic light-emitting device of the present invention, the light-emitting layer can be composed of only the condensed ring aromatic compound of the present invention. Further, the condensed ring aromatic compound of the present invention can be used as a guest (dopant) material or a host material. Furthermore, the condensed ring aromatic compound of the present invention can also be used as an electron transporting layer material.

Herein, when the condensed ring aromatic compound of the present invention is used as a guest material, an amount of the compound used is preferably 0.01% by weight to 20% by weight, more preferably 0.1% by weight to 15% by weight based on a host material. If the condensed ring aromatic compound of the present invention is used within this range, concentration quenching occurred by overlapping guest materials with each other in a light-emitting layer can be appropriately suppressed.

When the condensed ring aromatic compound of the present invention is used as a guest material, it is preferred that an energy gap of the host material is larger than that of the guest material.

In the present invention, the condensed ring aromatic compound of the present invention is especially used as a material for constituting a light-emitting layer, but can also be used together with, for example, low molecular-based and polymer-based hole transporting compounds, light-emitting compounds or electron transporting compounds which are conventionally known, if necessary.

Examples of the hole transporting compounds include triarylamine derivatives, phenylenediamine derivatives, triazole derivatives, oxadiazole derivatives, imidazole derivatives, pyrazoline derivatives, pyrazolone derivatives, oxazole derivatives, fluorenone derivatives, hydrazone derivatives, stilbene derivatives, phthalocyanine derivatives, porphyrin derivatives and poly(vinylcarbazole), poly(silylene), poly(thiophene) and other conductive polymers.

Examples of the light-emitting compounds include naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, rubrene derivatives etc., quinacridone derivatives, acridone derivatives, coumarin derivatives, pyran derivatives, nile red, pyrazine derivatives, a benzimidazole derivatives, benzothiazole derivatives, benzoxazole derivatives, stilbene derivatives, organic metal complexes (for example, organic aluminum complexes such as tris(8-quinolinolate)aluminum, organic beryllium complexes) and polymer derivatives such as poly(phenylenevinylene) derivatives, poly(fluorene) derivatives, poly(phenylene) derivatives, poly(thienylenevinylene) derivatives and poly(acetylene) derivatives, in addition to the condensed ring aromatic compound of the present invention.

Examples of the electron transporting compounds include oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives and organic metal complexes.

Examples of a material for constituting an anode include metal simple substances such as gold, platinum, silver, copper, nickel, palladium, cobalt, selenium, vanadium and tungsten, or an alloy of these metal simple substances, metal oxides such as tin oxide, zinc oxide, indium oxide, indium tin oxide (ITO) and indium zinc oxide. In addition, the material for constituting an anode also includes, for example, conductive polymers such as polyaniline, polypyrrol, polythiophene and polyphenylenesulfide. These electrode materials can be used singly or in combination of two or more of them. In addition, an anode may have a monolayer or multilayer structure.

Examples of a material for constituting a cathode include metal simple substances such as lithium, sodium, potassium, calcium, magnesium, aluminum, indium, ruthenium, titanium, manganese, yttrium, silver, lead, tin and chromium. Alternatively, the material for constituting a cathode includes, for example, two or more alloys such as lithium-indium, sodium-potassium, magnesium-silver, aluminum-lithium, aluminum-magnesium or magnesium-indium alloys, and also includes metal oxides such as indium tin oxide (ITO). These electrode materials can be used singly or in combination of two or more of them. In addition, a cathode may have a monolayer or multilayer structure.

Although a substrate used for the organic light-emitting device of the present invention is not particularly limited, for example, translucent substrates such as a metal substrate and a ceramic substrate, and transparent substrates such as glass, quartz and a plastic sheet are used.

Further, a luminescent color can also be controlled using, for example, a color filter film, a fluorescent color conversion filter film, a dielectric reflection film for a substrate. In addition, a device can also be fabricated by forming a thin film transistor (TFT) on a substrate and connecting it to the device.

Further, both a bottom emission structure (structure for taking out light from a substrate side) and a top emission structure (structure for taking out light from a side opposite to a substrate) can be employed with respect to the direction for taking out light of a device.

EXAMPLES

Hereinafter, the present invention will be further specifically described by means of examples, but should not be limited to these examples.

Example 1

Synthesis of Exemplified Compound H-6

(1-1) Synthesis of Synthetic Intermediate Compound 1-2

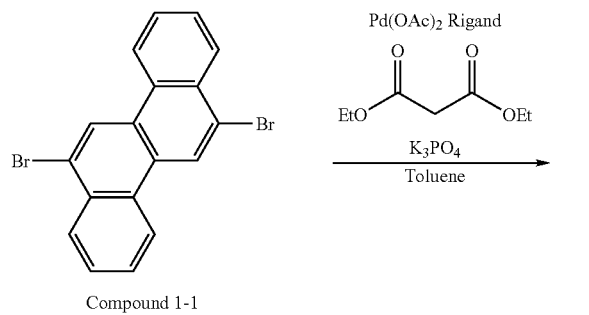

Compound 1-1

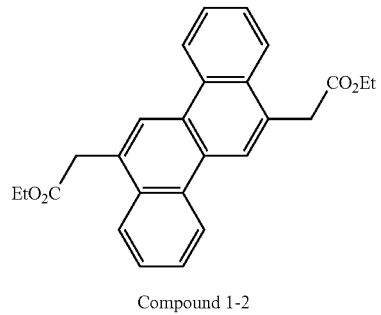

Compound 1-2

The reagents and solvents shown below were charged into a 300 ml recovery flask and stirred at 80° C. for 18 hours under nitrogen gas flow.
  Compound 1-1: 5.0 g (13.0 mmol)
  Ethyl acetoacetate: 6.74 g (51.8 mmol)
  Tripotassium phosphate: 16.5 g (77.7 mmol)
  Palladium acetate (II): 116 mg (0.52 mmol)
  2-(di-tert-butylphosphino)-2'-methylbiphenyl: 324 mg (1.04 mmol)
  Toluene: 100 ml
  Ethanol 15 ml After completion of the reaction, an organic layer of the reaction mixture was separated by adding toluene and water, and dried over magnesium sulfate, and thereafter the solvent was distilled off. The resulting product was purified by silica gel column chromatography (developing solvent: toluene/chloroform=1/1) to obtain 2.87 g of a compound 1-2 (yield: 55%).

(1-2) Synthesis of Synthetic Intermediate Compound 1-3

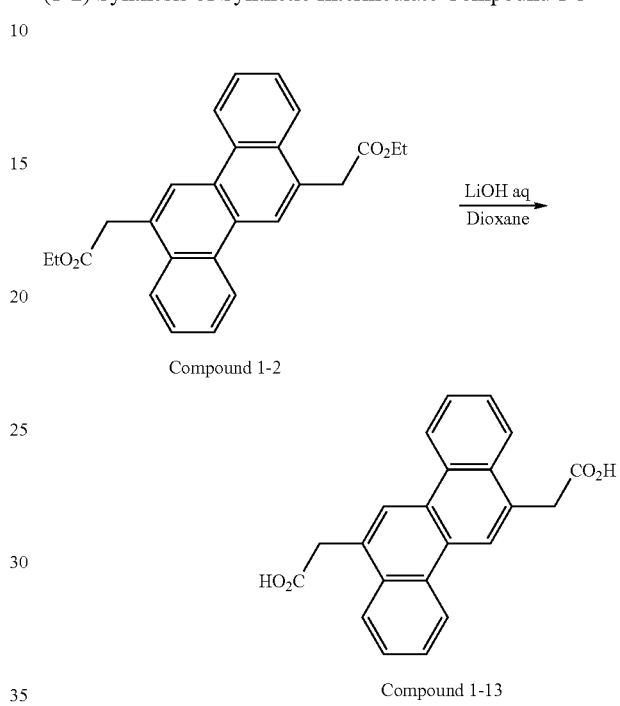

The reagents and solvents shown below were charged into a recovery flask and stirred at 90° C. for 24 hours.
  Compound 1-2: 3.76 g (89.6 mmol)
  Dioxane: 30 ml
  Lithium hydroxide monohydrate: 3.76 g (89.6 mmol)

Concentrated hydrochloric acid (20 ml) was slowly added to this suspension and the resulting mixture was stirred at room temperature for 5 hours. Thereafter, water (200 ml) was added to the mixture and the precipitated crystals were separated by filtration. The crystals were washed sequentially with water, methanol and diethyl ether, and then heated and dried under high vacuum to obtain 2.87 g of a compound 1-3 (yield: 93%).

(1-3) Synthesis of Synthetic Intermediate Compound 1-5

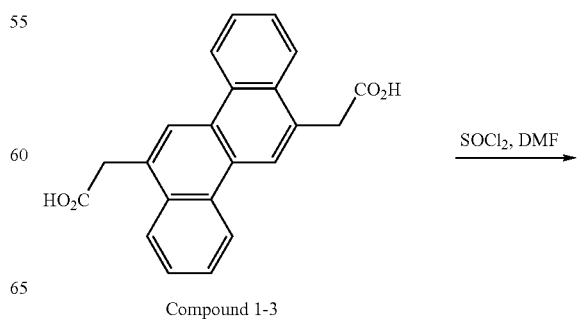

Compound 1-3

(1-4) Synthesis of Synthetic Intermediate Compound 1-6

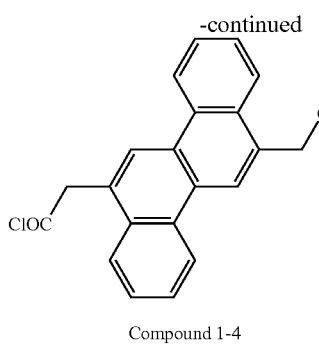

Compound 1-4

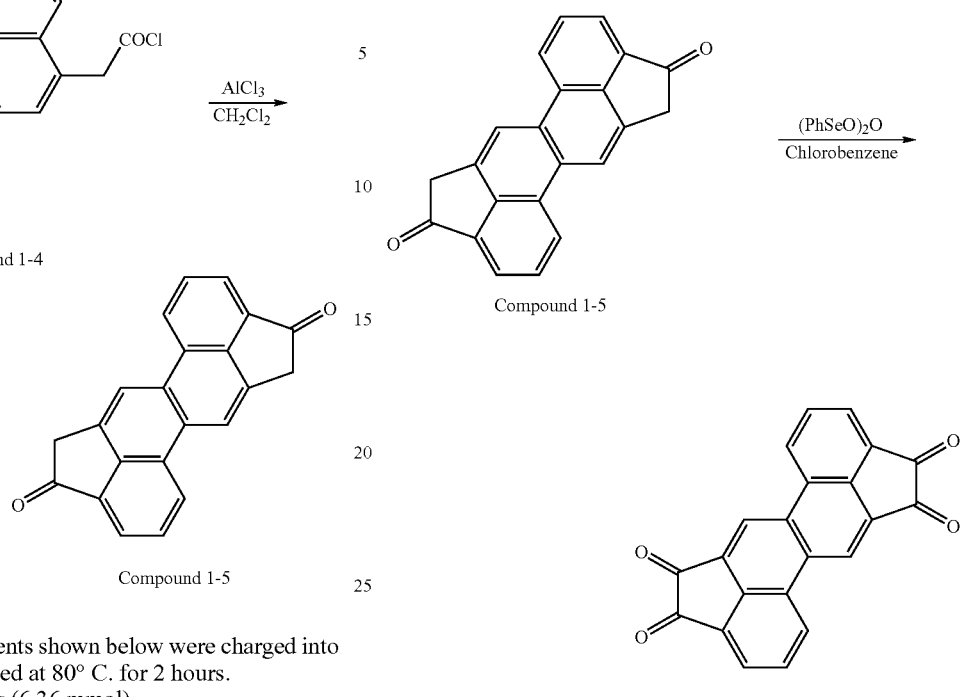

Compound 1-5

The reagents and solvents shown below were charged into a recovery flask and stirred at 80° C. for 2 hours.
  Compound 1-3: 2.87 g (6.36 mmol)
  Thionyl chloride: 50 ml
  Dimethylformamide: 300 μl
This suspension was distilled off under reduced pressure, and dichloromethane (50 ml) and trialuminum chloride (2.1 g, 15.9 mmol) were sequentially added to the resulting residue, and the mixture was vigorously stirred at room temperature for 18 hours. Concentrated hydrochloric acid (180 ml) was added to the resulting suspension, and the mixture was heated and stirred for 1 hour. This suspension was separated by filtration and the filtrate was subjected to Soxhlet extraction using chloroform as a solvent, and the resulting extract was concentrated. The extract was purified by silica gel column chromatography (developing solvent: chloroform/ethyl acetate=15/1) to obtain 1.2 g of a compound 1-5 (yield: 61%).

The reagents and solvents shown below were charged into a recovery flask and stirred at 130° C. for 18 hours.
  Compound 1-5: 1.2 g (3.89 mmol)
  Benzene selenic anhydride: 4.4 g (8.56 mmol)
  Chlorobenzene: 60 ml
This suspension was cooled to 100° C. and the crystals precipitated while still hot were separated by filtration. The obtained crystals were washed with hexane and dried under high vacuum to obtain 1.27 g of a compound 1-6 (yield: 97%).

(1-5) Synthesis of Synthetic Intermediate Compound 1-8

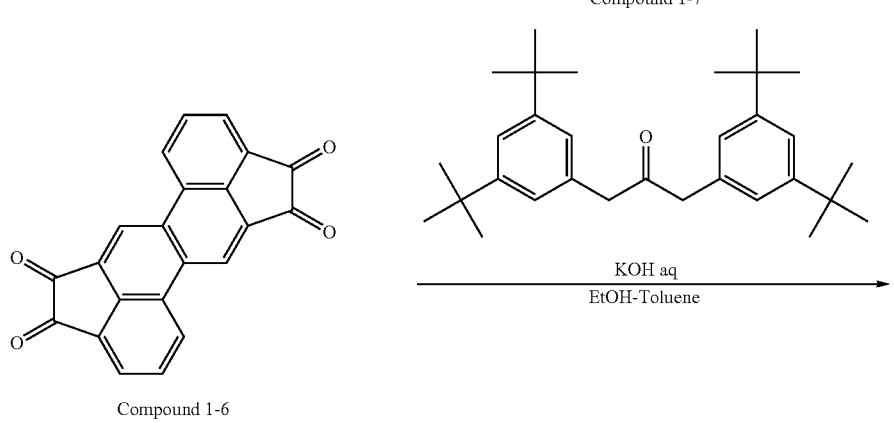

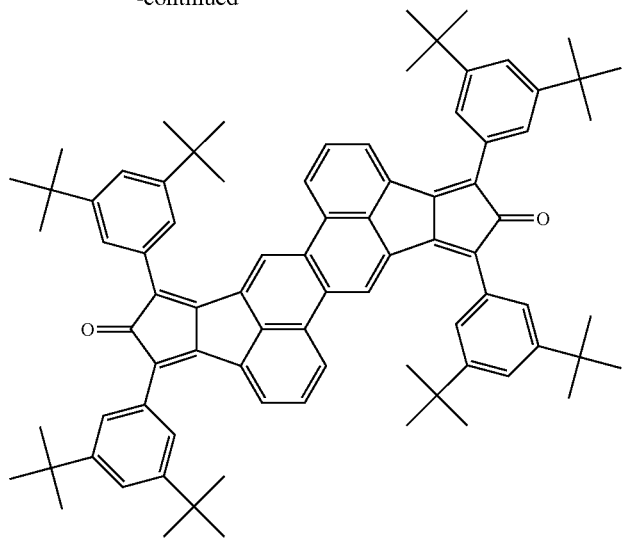

Compound 1-8

The reagents and solvents shown below were charged into a recovery flask and stirred at 80° C. for 18 hours under nitrogen gas flow.
  Compound 1-6: 37 mg (0.0046 mmol)
  Compound 1-7: 40 mg (0.0092 mmol)
  Ethanol: 2 ml
  Toluene: 0.4 ml
  6N-Potassium hydroxide: 300 μl
After completion of the reaction, the reaction mixture was left to cool to room temperature and the resulting crystals were separated by filtration. The crystals were washed with methanol and IPE (isopropyl ether) and dried under high vacuum to obtain 55 mg of a compound 1-8 (yield: 99%).

(1-6) Synthesis of Exemplified Compound H-6

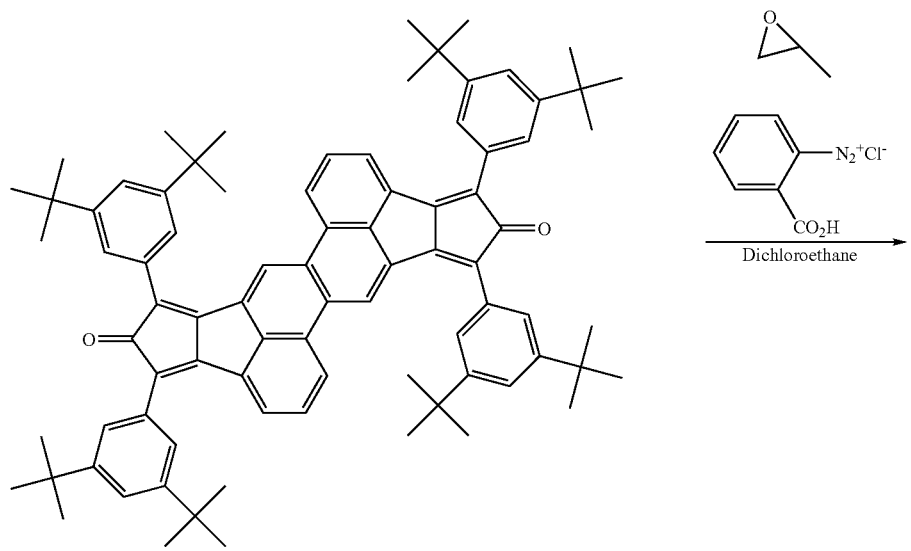

Compound 1-8

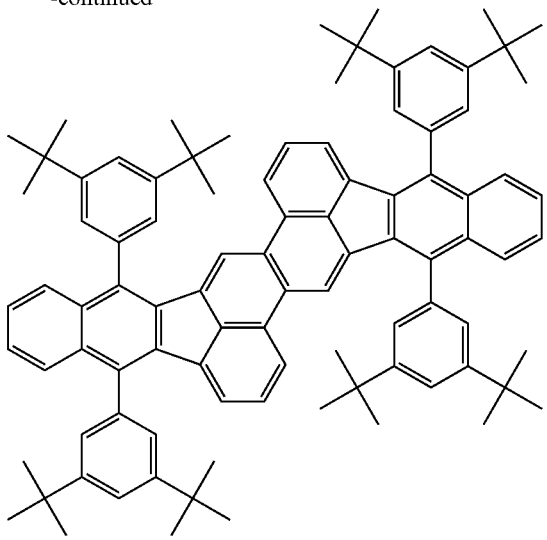

Exemplified Compound H-6

The reagents and solvents shown below were charged into a recovery flask and stirred at 70° C. for 5 hours.

Compound 1-8: 55 mg (0.0485 mmol)
Benzene diazonium-2-carboxylate hydrochloride: 500 mg (0.27 mmol)
Propylene oxide: 0.5 ml
Dichloroethane: 5 ml After completion of the reaction, the reaction mixture was left to cool to room temperature and the resulting crystals were separated by filtration. The crystals were sufficiently washed with diethyl ether-hexane, and then purified by silica gel column chromatography (developing solvent: hexane/chloroform=3/1) to obtain 33 mg of an exemplified compound H-6 (yield: 55%).

The physical properties of the obtained compound were measured and evaluated.

(Molecular Weight)

The compound was confirmed to have M+ of 1229.79 by MALDI-TOF-MS (Matrix-assisted laser desorption/ionization time-of-flight mass spectrometry) and thus identified to be an exemplified compound H-6.

(NMR)

The structure of this compound was confirmed by NMR measurement.

$^1$H-NMR (CDCl3, 400 MHz) σ (ppm):7.87-7.86 (m, 4H), 7.78-7.77 (m, 2H), 7.73 (d, 2H, J=8.0 Hz), 7.66 (t, 2H, J=2.0 Hz), 7.48-7.41 (m, 14H), 7.35 (t, 2H, J=7.6 Hz), 6.65 (d, 2H, J=7.2 Hz), 1.42 (s, 36H), 1.39 (s, 36H)

(Light-Emitting Characteristics)

Figure 6:
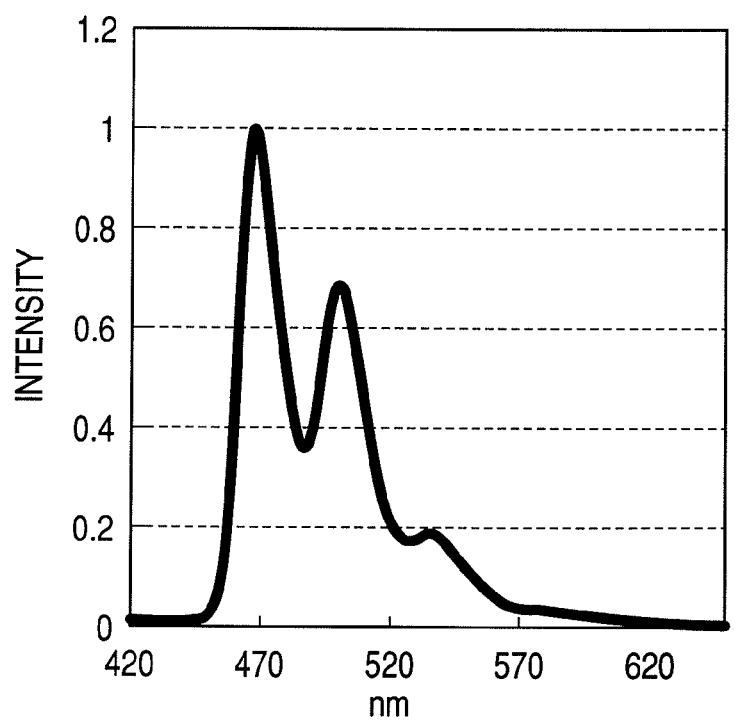
FIG. 6 is a graph showing a PL spectrum (excitation wavelength: 351 nm) of a toluene solution of an exemplified compound H-6 ($1 \times 10^{-5}$ mol/L).

The emission spectrum of the exemplified compound H-6 in a solution form was measured. Before measurement of the emission spectrum, the absorption spectrum of a toluene solution of the exemplified compound H-6 ($1 \times 10^{-5}$ mol/L) was previously measured using a spectrophotometer "U-3010" (manufactured by Hitachi High-Technologies Corporation). After measuring the absorption spectrum, the emission spectrum (PL spectrum) of the toluene solution of the exemplified compound H-6 ($1 \times 10^{-5}$ mol/L) was measured using a fluorescence spectrophotometer "F-4500" (manufactured by Hitachi High-Technologies Corporation). In this case, the excitation wavelength was set at 351 nm from the results of absorption spectrum measurement. As a result of measurement, PL spectrum shown in FIG. 6 was obtained. It was found from the PL spectrum shown in FIG. 6 that the maximum wavelength of the exemplified compound H-6 had a first peak and a second peak of 469 nm and 502 nm, respectively, and the compound H-6 exhibited good blue emission.

Example 2

Synthesis of Exemplified Compound H-1

(2-1) Synthesis of Synthetic Intermediate Compound 1-10

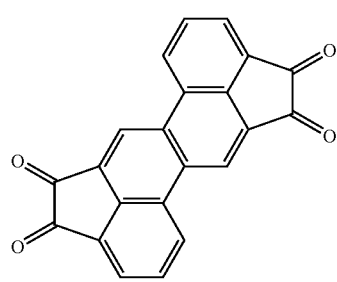

Compound 1-6

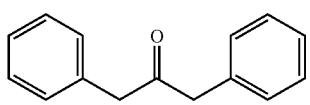

Compound 1-9

KOH aq
EtOH-Toluene

Compound 1-10

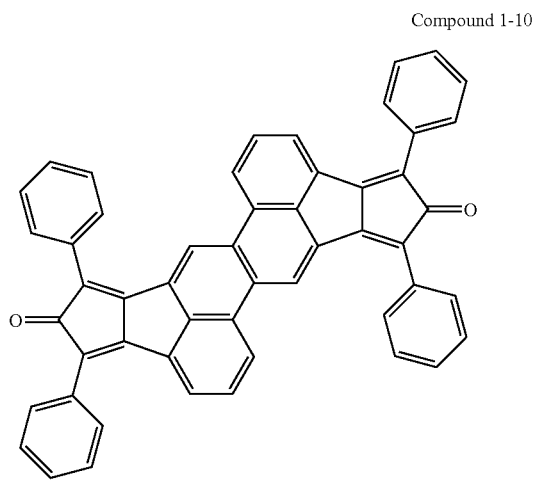

-continued

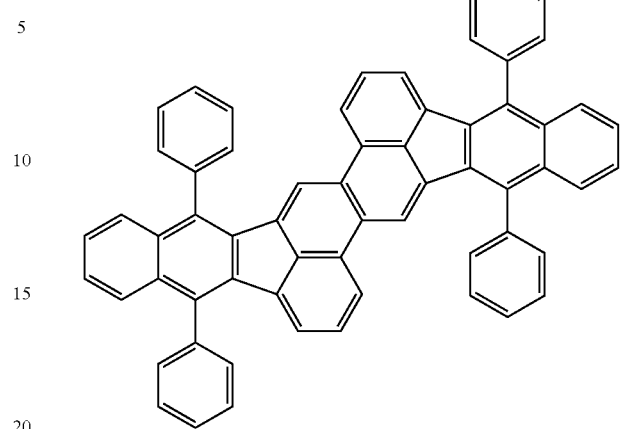

Exemplified
Compound H-1

The reagents and solvents shown below were charged into a recovery flask and stirred at 80° C. for 0.5 hours under nitrogen gas flow.

Compound 1-6: 0.76 g (2.26 mmol)
Compound 1-9: 0.8 g (3.80 mmol)
Ethanol 18 ml
Toluene: 2 ml
6N-Potassium hydroxide: 800 ml After completion of the reaction, the reaction mixture was left to cool to room temperature and the resulting crystals were separated by filtration. The crystals were washed with methanol and IPE and dried under high vacuum to obtain 330 mg of a compound 1-10 (yield: 21%).

(2-2) Synthesis of Exemplified Compound H-1

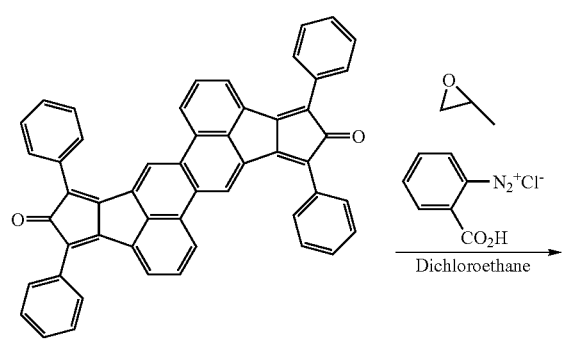

Compound 1-10

The reagents and solvents shown below were charged into a recovery flask and stirred at 70° C. for 2 hours.

Compound 1-10: 76 mg (0.111 mmol)
Benzene diazonium-2-carboxylate hydrochloride: 82 mg (0.444 mmol)
Propylene oxide: 0.2 ml
Dichloroethane: 4 ml After completion of the reaction, the reaction mixture was left to cool to room temperature and the resulting crystals were separated by filtration. The crystals were sufficiently washed with diethyl ether, and then purified by silica gel column chromatography (developing solvent: hexane/chloroform=3/1) to obtain 45 mg of an exemplified compound H-1 (yield: 51%).

The physical properties of the obtained compound were measured and evaluated.

(Molecular Weight)

The compound was confirmed to have M+ of 780.04 by MALDI-TOF-MS (Matrix-assisted laser desorption/ionization time-of-flight mass spectrometry) and thus identified to be an exemplified compound H-1.

(NMR)

The structure of this compound was confirmed by NMR measurement.

$^1$H-NMR (CDCl3, 400 MHz) σ (ppm): 7.81 (t, 6H, J=2.8 Hz), 7.73-7.65 (m, 18H), 7.60-7.58 (m, 4H), 7.43-7.38 (m, 6H), 7.54 (d, 2H, J=6.8 Hz), 1.42 (s, 36H), 1.40 (s, 36H)

Hereinafter, each of exemplified compounds H-3, H-5, H-7 and I-1 can be synthesized by the same synthesis method as in Example 1. Specifically, the synthesis was performed under the same conditions as in Example 1 except that a dibromochrysene derivative and an acetone derivative shown in Table 1 below are used in place of the compound 1-1 and the compound 1-7, respectively, in Example 1.

TABLE 1
| Exemplified Compound | Dibromochrysene derivative | Acetone derivative |
| --- | --- | --- |
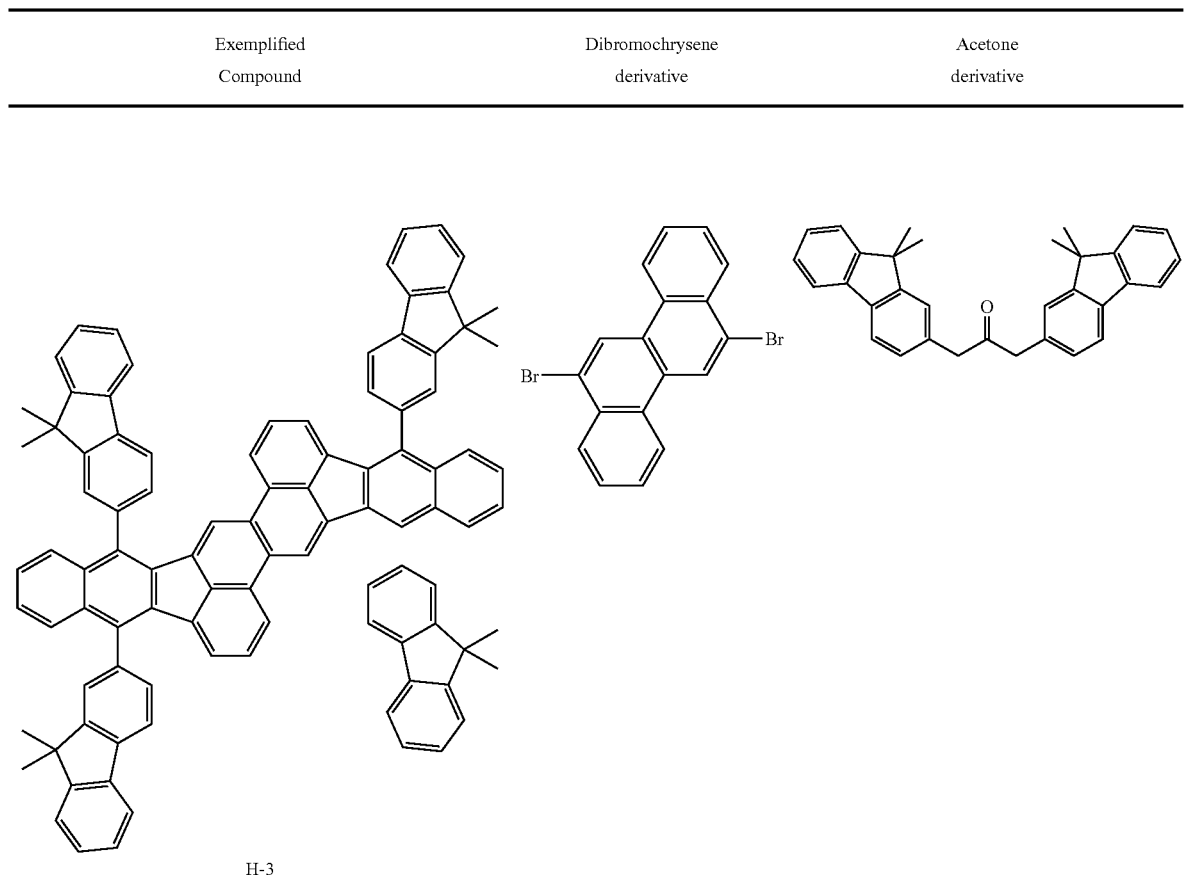
H-3
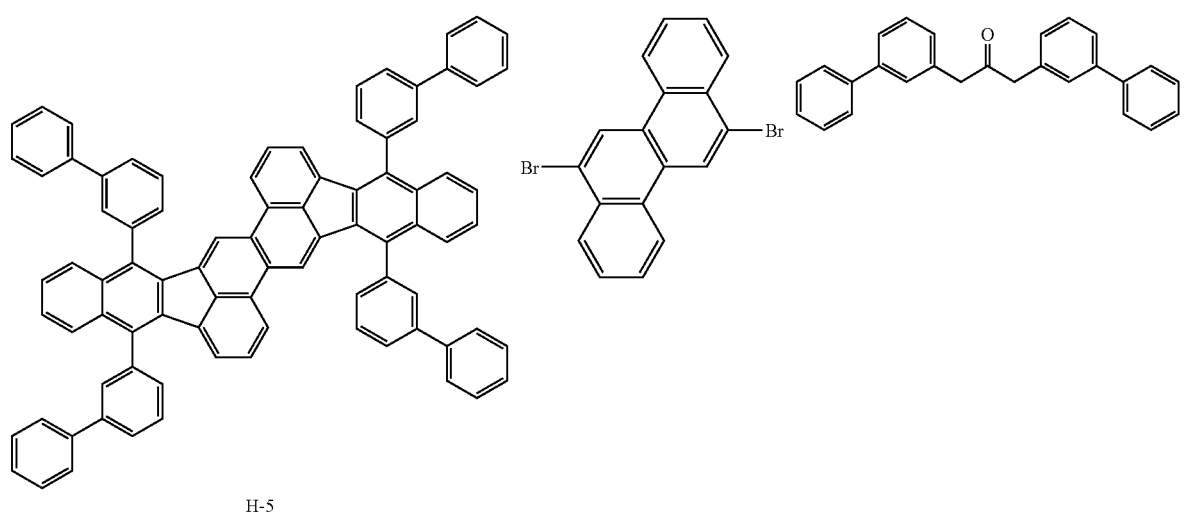
H-5

TABLE 1-continued

| Exemplified Compound | Dibromochrysene derivative | Acetone derivative |
|---|---|---|
| 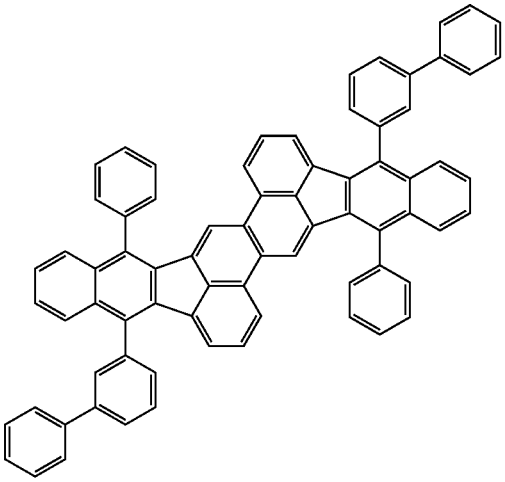 H-7 | 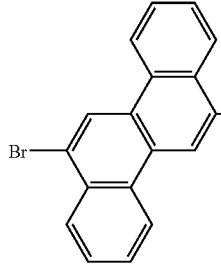 | 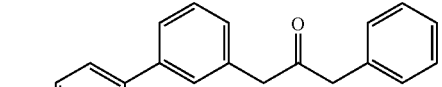 |
| 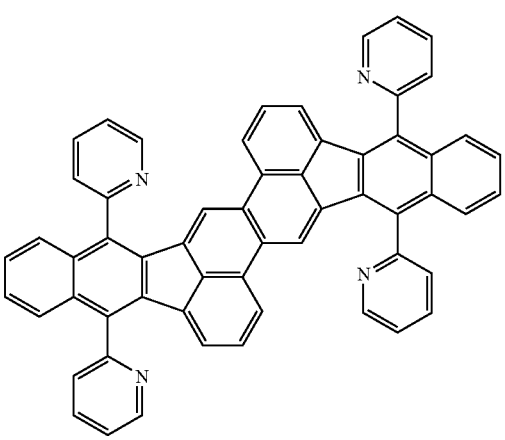 I-1 | 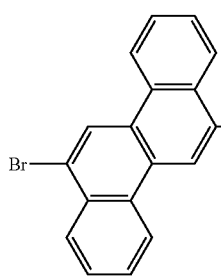 | 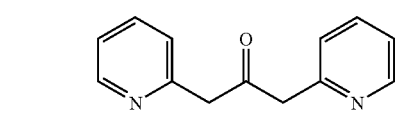 |

Further, each of exemplified compounds B-1, C-3, D-1, E-1, F-1, G-2, H-2, I-3 and J-2 can be synthesized by a method of the synthesis route 1. Specifically, as a dibromochrysene derivative and a boronic acid derivative in the synthesis route 1, the compounds shown in the Table 2 below corresponding to each of the derivatives are used.

TABLE 2

| Exemplified Compound | Dibromochrysene derivative | Boronic acid derivative |
|---|---|---|
| 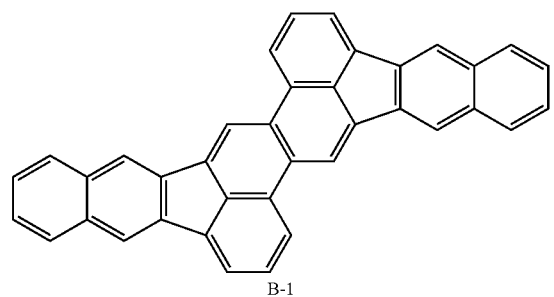 B-1 | 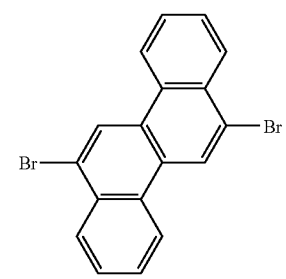 | 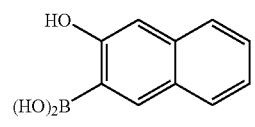 |

TABLE 2-continued
| Exemplified Compound | Dibromochrysene derivative | Boronic acid derivative |
|---|---|---|
| 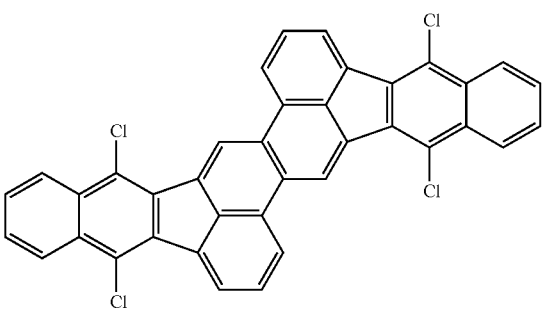<br>C-3 | 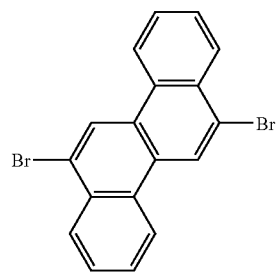 | 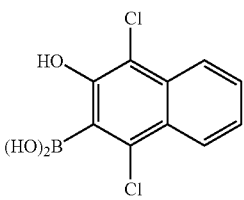 |
| 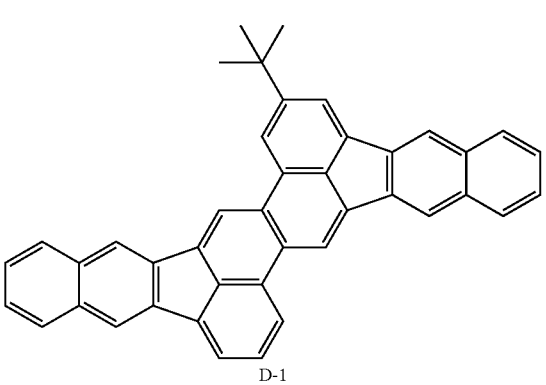<br>D-1 | 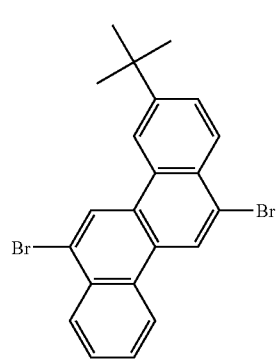 | 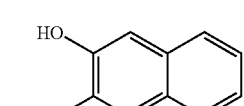 |
| 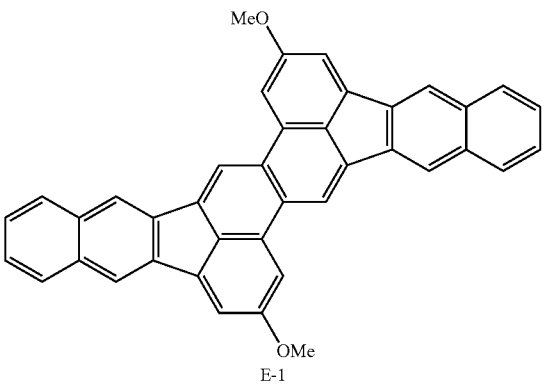<br>E-1 | 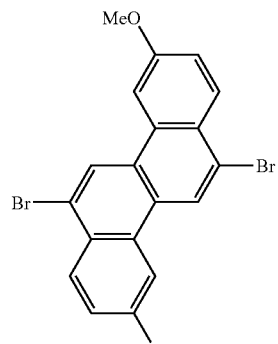 | 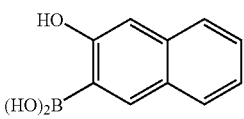 |
| 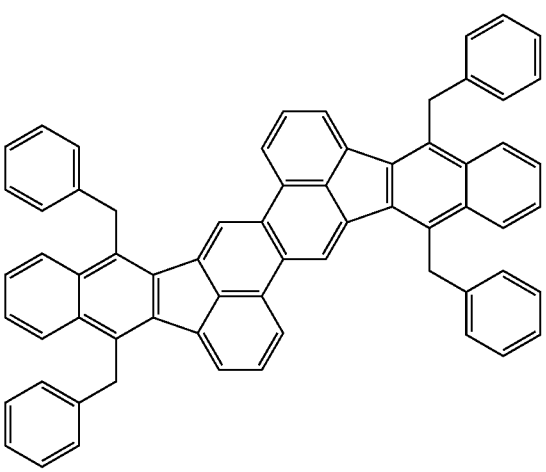<br>F-1 | 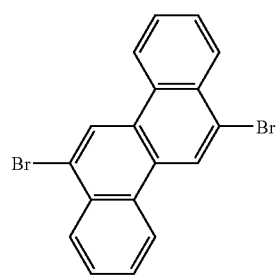 | 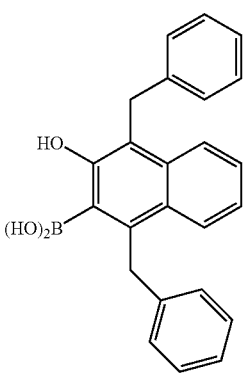 |

TABLE 2-continued
| Exemplified Compound | Dibromochrysene derivative | Boronic acid derivative |
| --- | --- | --- |
| 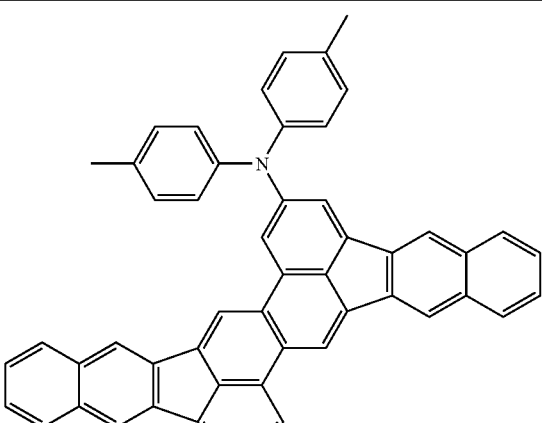<br>G-2 | 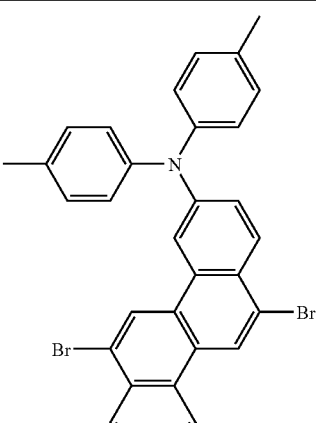 | 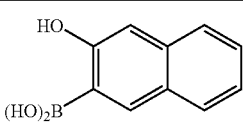 |
| 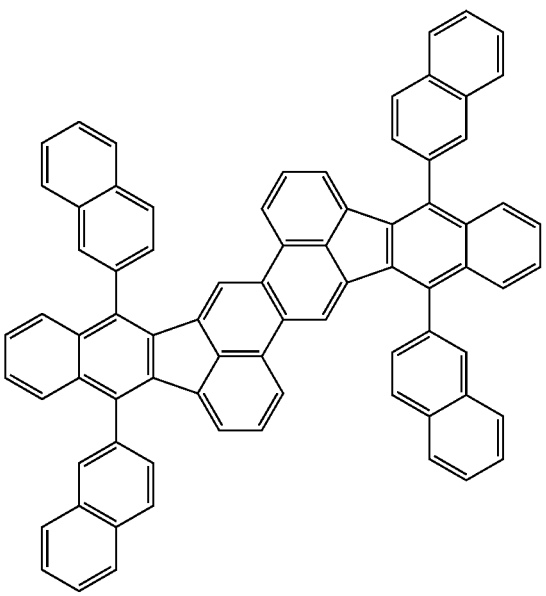<br>H-2 | 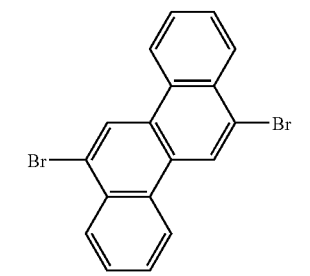 | 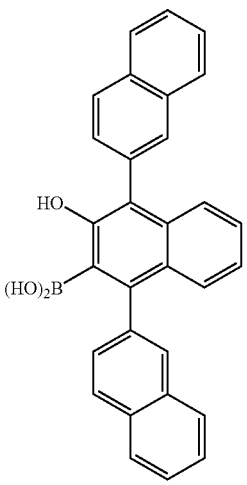 |
| 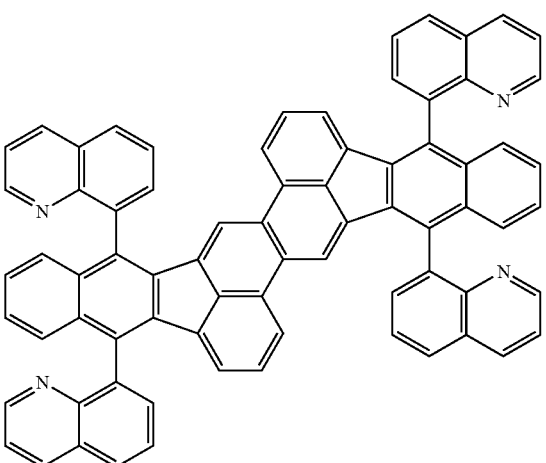<br>I-3 | 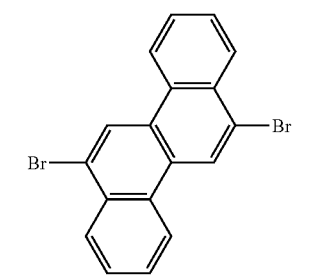 | 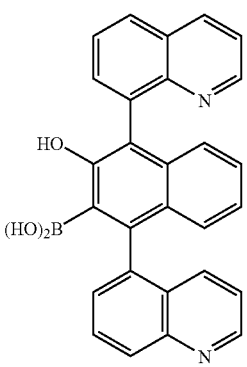 |

TABLE 2-continued

| Exemplified Compound | Dibromochrysene derivative | Boronic acid derivative |
|---|---|---|
| 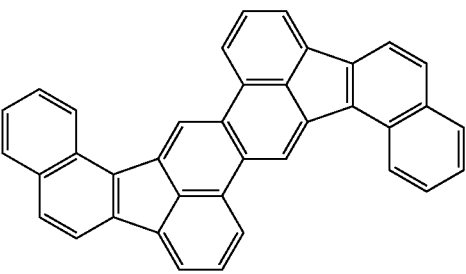 J-2 | 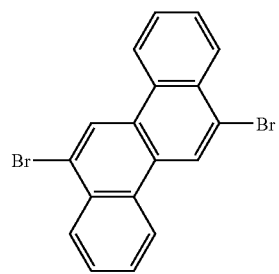 | 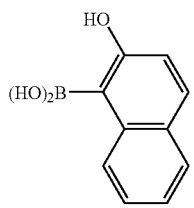 |

Example 6

Fabrication of Organic Light-Emitting Device

The organic light-emitting device shown in FIG. 3 was fabricated in this Example. Firstly, indium tin oxide (ITO) (an anode 2) was patterned to have a film thickness of 100 nm on a glass substrate (a substrate 1), and thereby a glass substrate with an ITO electrode was fabricated. Next, a layer comprising an organic compound and a cathode were subjected to vacuum evaporation using resistance heating to continuously form a film on this glass substrate with an ITO electrode. Specifically, at first, a compound 2 shown below was used as a hole transporting layer 5 to form a film with a thickness of 20 nm. Then, a compound 3 shown below serving as a host and the exemplified compound H-1 serving as a guest were co-evaporated as a light-emitting layer 3 so that a content of the exemplified compound H-1 was 1% by weight based on the compound 3. In this case, the light-emitting layer 3 was formed to have a film thickness of 30 nm. Successively, a compound 4 shown below was used as an electron transporting layer to form a film with a thickness of 30 nm. Thereafter, KF was used to form a film with a thickness of 1 nm, and finally aluminum was used to form a film with a thickness of 100 nm. Here, KF and aluminum function as a cathode 4.

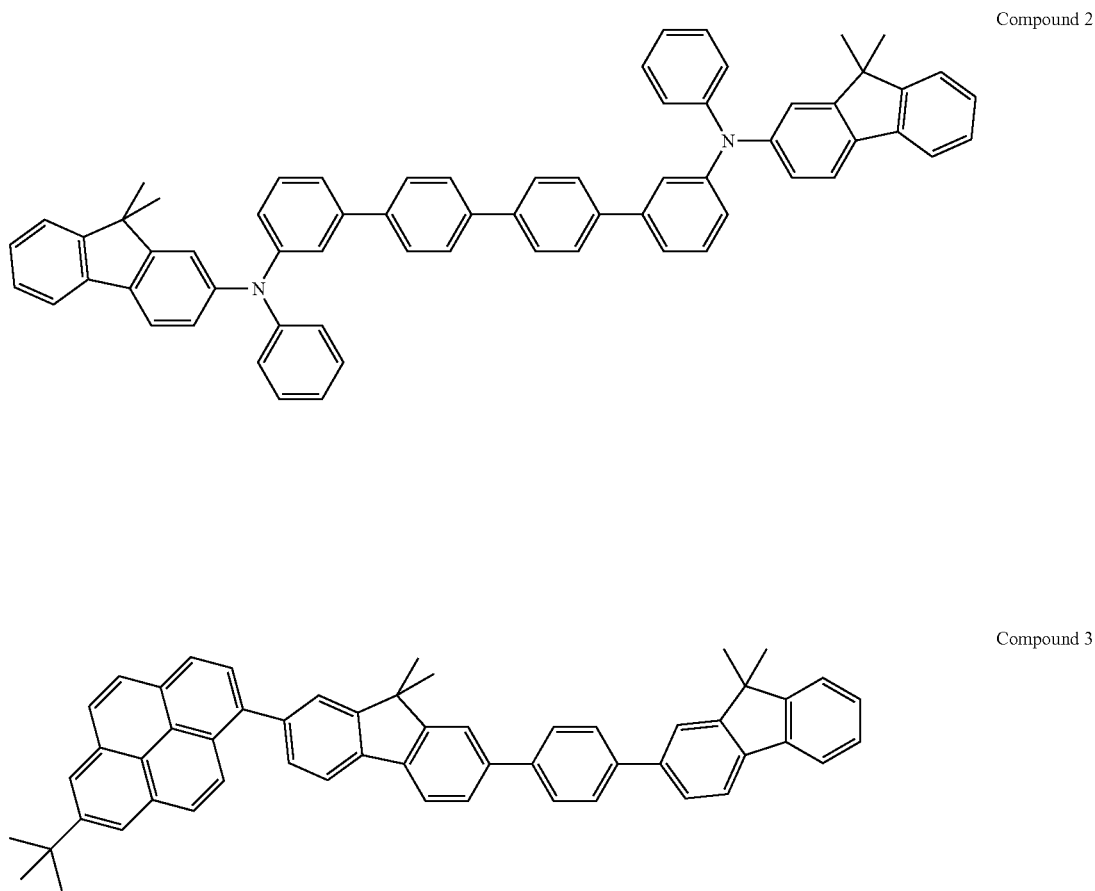

Compound 2

Compound 3

-continued

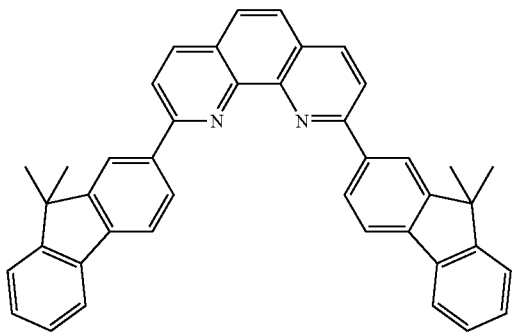

Compound 4

It is to be noted that the pressure in a vacuum chamber was set at $10^{-5}$ Pa during film formation. In addition, when fabricating a device, each of electrodes opposed to each other was formed to have an area of 3 mm². As described above, the organic light-emitting device was obtained.

The physical properties of the obtained organic light-emitting device were measured and evaluated. Specifically, the current-voltage characteristics and the emission luminance of the device were measured by a microammeter "4140B" manufactured by Hewlett-Packard Development Company, L.P and a luminance meter "BM 7" manufactured by Topcon Corporation, respectively. As a result, the organic light-emitting device showed an emission luminance of 300 cd/m² at an applied voltage of 4.0 V and blue emission was observed. Further, it was confirmed that the device was maintained at a current density of 30 mA/cm² under a nitrogen atmosphere and exhibited good durability after driven by applying a voltage for 100 hours.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2007-096343, filed Apr. 2, 2007 and 2008-038298, filed Feb. 20, 2008, which are hereby incorporated by reference herein in their entirety.

The invention claimed is:

1. A condensed ring aromatic compound represented by the following general formula [1]:

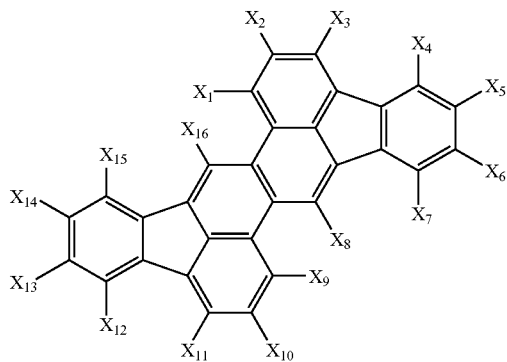

wherein $X_1$ to $X_{16}$ each independently represent a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and each may be the same or different; adjacent groups combine with each other to form at least one ring in the group selected from $X_4$ to $X_7$; and adjacent groups combine with each other to form at least one ring in the group selected from $X_{12}$ to $X_{15}$.

2. The condensed ring aromatic compound according to claim 1, represented by the following general formula [2]:

[2]

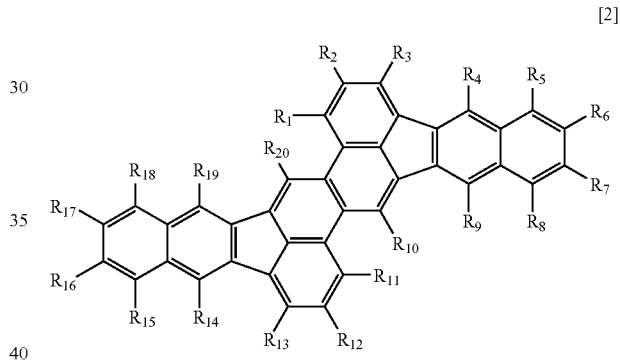

wherein $R_1$ to $R_{20}$ each independently represent a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and each may be the same or different.

3. An organic light-emitting device including:
   a pair of electrodes comprising an anode and a cathode of which at least one is transparent or translucent; and
   an organic compound layer disposed between the pair of electrodes, wherein the organic compound layer contains the condensed ring aromatic compound according to claim 1.

4. The organic light-emitting device according to claim 3, wherein the organic compound layer is a light-emitting layer.

5. An organic light-emitting device including:
   a pair of electrodes comprising an anode and a cathode of which at least one is transparent or translucent; and
   an organic compound layer disposed between the pair of electrodes, wherein the organic compound layer contains the condensed ring aromatic compound according to claim 2.

6. The organic light-emitting device according to claim 5, wherein the organic compound layer is a light-emitting layer.

* * * * *